US012675308B2

(12) United States Patent
Nair

(10) Patent No.: US 12,675,308 B2
(45) Date of Patent: Jul. 7, 2026

(54) DYNAMIC I/O VIRTUALIZATION SYSTEM HAVING GUEST MEMORY MANAGEMENT FOR MAPPING VIRTUAL ADDRESSES MANAGED BY PROCESS AND MEMORY MANAGER (PMM) AND DYNAMIC EXECUTION CONTEXT (DEC)

(71) Applicant: Dynavisor, Inc., Milpitas, CA (US)

(72) Inventor: Sreekumar R. Nair, San Jose, CA (US)

(73) Assignee: Dynavisor, Inc., Milpitas, CA (US)

( * ) Notice: Subject to any disclaimer, the term of this patent is extended or adjusted under 35 U.S.C. 154(b) by 0 days.

(21) Appl. No.: 18/800,873

(22) Filed: Aug. 12, 2024

(65) Prior Publication Data

US 2024/0403091 A1 Dec. 5, 2024

Related U.S. Application Data

(63) Continuation of application No. 18/460,374, filed on Sep. 1, 2023, now Pat. No. 12,061,919, which is a
(Continued)

(51) Int. Cl.
*G06F 3/00* (2006.01)
*C07K 16/28* (2006.01)
(Continued)

(52) U.S. Cl.
CPC ...... *G06F 9/45533* (2013.01); *C07K 16/2803* (2013.01); *C07K 16/2887* (2013.01); *C07K 16/2896* (2013.01); *G06F 3/061* (2013.01); *G06F 3/0664* (2013.01); *G06F 3/0665* (2013.01); *G06F 3/0685* (2013.01); *G06F*

*3/0689* (2013.01); *G06F 9/45558* (2013.01); *G06F 12/0868* (2013.01);
(Continued)

(58) Field of Classification Search
CPC .... G06F 9/45533; G06F 3/061; G06F 3/0664; G06F 9/45558; G06F 12/0868; G06F 13/28; G06F 3/00; G06F 9/00
See application file for complete search history.

(56) References Cited

U.S. PATENT DOCUMENTS 8,627,315 B2 * 1/2014 Li ....................... G06F 9/45533
709/224
2012/0102491 A1 * 4/2012 Maharana ........... G06F 13/4282
718/1
(Continued)

*Primary Examiner* — Tammara R Peyton
(74) *Attorney, Agent, or Firm* — Foley & Lardner LLP

(57) ABSTRACT

A system and method for providing dynamic I/O virtualization is herein disclosed. According to one embodiment, a device capable of performing hypervisor-agnostic and device-agnostic I/O virtualization includes a host computer interface, memory, I/O devices (GPU, disk, NIC), and efficient communication mechanisms for virtual machines to communicate their intention to perform I/O operations on the device. According to one embodiment, the communication mechanism may use shared memory. According to some embodiments, the device may be implemented purely in hardware, in software, or using a combination of hardware and software. According to some embodiments, the device may share its memory with guest processes to perform optimizations including but not limited to a shared page cache and a shared heap.

30 Claims, 12 Drawing Sheets

Related U.S. Application Data continuation of application No. 17/518,859, filed on Nov. 4, 2021, now Pat. No. 11,775,325, which is a continuation of application No. 16/744,773, filed on Jan. 16, 2020, now Pat. No. 11,175,936, which is a continuation of application No. 16/128,913, filed on Sep. 12, 2018, now Pat. No. 10,635,469, which is a continuation of application No. 15/880,092, filed on Jan. 25, 2018, now Pat. No. 10,255,087, which is a continuation of application No. 14/555,473, filed on Nov. 26, 2014, now Pat. No. 9,910,689.

(51) Int. Cl.

| | | |
|---|---|---|
| *G06F 3/06* | (2006.01) | |
| *G06F 9/00* | (2018.01) | |
| *G06F 9/455* | (2018.01) | |
| *G06F 12/0868* | (2016.01) | |
| *G06F 12/1081* | (2016.01) | |
| *G06F 13/28* | (2006.01) | |
| *A61K 39/00* | (2006.01) | |
| *G06F 9/4401* | (2018.01) | |
| *G06F 12/084* | (2016.01) | |
| *G06F 12/0864* | (2016.01) | |

(52) U.S. Cl.

CPC .......... *G06F 12/1081* (2013.01); *G06F 13/28* (2013.01); *A61K 2039/505* (2013.01); *A61K 2039/507* (2013.01); *C07K 2317/21* (2013.01); *C07K 2317/24* (2013.01); *C07K 2317/33* (2013.01); *C07K 2317/52* (2013.01); *C07K 2317/56* (2013.01); *C07K 2317/565* (2013.01); *C07K 2317/73* (2013.01); *C07K 2317/76* (2013.01); *G06F 3/0673* (2013.01); *G06F 9/4411* (2013.01); *G06F 2009/45579* (2013.01); *G06F 12/084* (2013.01); *G06F 12/0864* (2013.01); *G06F 2212/152* (2013.01); *G06F 2212/2532* (2013.01); *G06F 2212/314* (2013.01); *G06F 2212/463* (2013.01)

(56) References Cited

U.S. PATENT DOCUMENTS

| | | | |
|---|---|---|---|
| 2012/0284712 A1* | 11/2012 | Nimmagadda | G06F 13/105 718/1 |
| 2013/0282994 A1* | 10/2013 | Wires | G06F 3/0604 709/212 |

* cited by examiner

DYNAMIC I/O VIRTUALIZATION SYSTEM HAVING GUEST MEMORY MANAGEMENT FOR MAPPING VIRTUAL ADDRESSES MANAGED BY PROCESS AND MEMORY MANAGER (PMM) AND DYNAMIC EXECUTION CONTEXT (DEC)

This application is a continuation of and claims priority to U.S. application Ser. No. 18/460,374, filed Sep. 1, 2023, which is a continuation of and claims priority to U.S. application Ser. No. 17/518,859, filed Nov. 4, 2021, now U.S. Pat. No. 11,775,325, which is a continuation of and claims priority to U.S. application Ser. No. 16/744,773, filed Jan. 16, 2020, now U.S. Pat. No. 11,175,936, which is a continuation of and claims priority to U.S. application Ser. No. 16/128,913, filed Sep. 12, 2018, now U.S. Pat. No. 10,635,469, which is a continuation of and claims priority to U.S. application Ser. No. 15/880,092, filed Jan. 25, 2018, now U.S. Pat. No. 10,255,087, which is a continuation of and claims priority to U.S. patent application Ser. No. 14/555,473, filed Nov. 26, 2014, now U.S. Pat. No. 9,910,689, which claims priority to U.S. Provisional patent application Ser. No. 61/909,324, filed Nov. 26, 2013, the entire disclosures of which are hereby incorporated by reference.

FIELD

The present disclosure relates in general to the field of computer software and systems, and in particular, to a system and method for dynamic I/O virtualization.

BACKGROUND

In a computer system, the term virtualization means hiding an implementation of components or abstracting details. In a rudimentary computing environment of a single tasking, one single program (or task) controls the entire computer system.

With the advent of multi-tasking computers, an operating system (OS) facilitated the efficient sharing of hardware devices across multiple tasks. An OS primarily provides functionalities for process management, memory management, and device management. For process management, an OS runs one task at a time on a central processing unit (CPU) for a predetermined quantum of time until the task is preempted by the OS to relinquish the CPU time for another task at the end of the predetermined time. For memory management, regardless of the size of the physical memory available on the computer system, the OS allows each task to have the full addressable range of memory, so that each task can address the entire address space. The mapping of physical addresses to virtual addresses of a given task is controlled by a kernel of the OS through a mechanism referred to as demand paging. During the execution of a task, all references to the code and data locations are given with respect to their virtual addresses. In early computer architectures, the translation of virtual address to physical address was performed in software, therefore the translation was painstakingly slow.

To overcome the performance limitation of software virtual address translation, processors (e.g., INTEL® i386) started to use hardware page tables to transparently perform the translation between virtual addresses and physical addresses. To facilitate faster context switching between the user process and the OS kernel via system calls, many OS'es such as Linux started to map the kernel virtual address space into the address space of the task itself. For instance, in 32-bit Linux, three-fourths of memory (0x00000000 through 0xbfffffff) is assigned for the user address space and one-fourth of memory (0xc0000000 through 0xffffffff) is assigned for the kernel address space.

The OS permits that each task has an exclusive control over CPU and memory during the time slice of its execution. However, for other devices such as graphics processing unit (GPU), storage devices, network interface card (NIC), the OS directly manages these devices and exercises discretion to ensure the appropriate use of these devices. For example, some devices may need to be exclusively used by one task (e.g., a printer), while others may be concurrently shared among multiple tasks. Some device operations need to be performed atomically while others may be interleaved.

S/360 system by IBM® launched in 1964 was the first attempt of system virtualization of the physical computer. System virtualization makes multiple instances of guest OS'es to run on the same hardware by a supervisory software layer called a hypervisor or a virtual machine manager (VMM). The hypervisor or VMM is interchangeably referred to as a host. Original system virtualization ran the OS in a de-privileged mode (i.e., non-supervisor mode). Based on their mode of deployment, hypervisors are classified into two types. Type 1 hypervisor boots directly on the bare metal (like a classical OS) and brings up the guest OS'es on top of the hypervisor layer. Examples of type 1 hypervisor include, but are not limited to, VMWARE® ESX hypervisor and XEN® hypervisor. Type 2 hypervisor, also referred to as a hosted hypervisor, runs inside a host OS that boots on the bare metal but the actual hypervisor is a user-mode component. Examples of type 2 hypervisor include, but are not limited to, VMWARE® Desktop, and Kernel Virtual Machine (KVM), and FreeBSD BHyVe.

During the early days of system virtualization, compute virtualization, i.e., virtualization of CPU and memory, posed technical challenges. For CPU virtualization of INTEL®/AMD® x86, when an OS runs in a de-privileged level, some sensitive instructions behave differently in the lower privilege levels without faulting. If such instructions had faulted (as happens in "trap-and-emulate" processor architectures), the hypervisor or host would get the opportunity to control and fix the anomaly. For example, if the OS runs in a lower privilege (e.g., Ring 1) than the designated privilege level (e.g., Ring 0), the processor simply executes these sensitive x86 instructions in Ring 1 with different semantics instead of faulting. Dynamic translation and OS paravirtualization techniques were devised to deal with such sensitive instructions. Later processor manufacturers (e.g., INTEL®, AMD®) came up with efficient hardware architectures to handle CPU virtualization, for example, INTEL® virtualization technology (VT) and AMD-V, wherein such sensitive instructions raise a special trap giving control to the hypervisor to enforce the correct semantics of these instructions.

For memory virtualization, a guest virtual address that is translated to a guest physical address requires an additional level of translation to access physical memory destination of the host. Efficient hardware architectures such as INTEL® extended page table (EPT) and AMD® nested page table (NPT) address memory virtualization by providing hardware support for translating guest virtual address directly to host physical address.

After the compute virtualization was harnessed with efficient hardware architecture, the focus of the computing industry shifted to I/O virtualization. I/O virtualization involves virtualization of devices such as GPUs, storage devices, and NICs. Depending on the deployment type for system virtualization, there are three tiers of I/O virtualizations.

Tier 1 I/O virtualization is connectivity virtualization. Tier 1 I/O virtualization focuses on the optimization of the data center floor to improve the efficiency of physical connectivity, cabling, routing/switching, power distribution etc. For example, XSIGO® data center fabric minimizes physical connections across servers and provides a high speed and low-latency interconnect among servers.

Tier 2 I/O virtualization is hardware device virtualization. Tier 2 I/O virtualization focuses on making multiple virtual hardware endpoints available for use across multiple physical servers. Peripheral Component Interconnect Special Interest Group (PCI-SIG) defines standards for single root I/O virtualization (SR-IOV) and multi root I/O virtualization (MR-IOV). Both SR-IOV and MR-IOV aim at making single physical devices such as a GPU or NIC behave as if they are composed of multiple logical devices. Each of the multiple logical devices of a physical device, referred to as virtual functions (VFs), appears to OS'es as a virtual device such as an individual GPU or NIC. Each VF is exclusively assigned to a guest OS. Tier 2 I/O virtualization also involves PCI Express (PCIe) virtualization, for example, VirtenSys and Aprius. VirtenSys extends PCIe bus outside a group of servers to a switch from which PCIe-connected peripherals such as Ethernet NICs and fiber channel HBAs are shared by the servers, avoiding each of them requiring their own NIC and HBA. Aprius allows servers to share peripheral devices at PCIe bus speeds over a virtual PCIe bus network.

Tier 3 I/O virtualization is software device virtualization that runs inside the server boxes based on hypervisors or VMMs. Tier 3 I/O virtualization focuses on enhancing the overall scalability and utilization of devices like GPUs, storage devices and NICs. Tier 3 I/O virtualization enables concurrent use of I/O devices by multiple guest OS'es.

Initially, tier 3 I/O virtualization used to emulate hardware devices in software. A virtual device driver that is loaded into a guest OS emulates device operations in software by communicating with a software layer in the host (e.g., a hypervisor). The virtual device driver cooperates with the native device drivers of the host to perform the I/O operations. Software device virtualization is generally slow because virtual device drivers are not designed to exploit device-specific optimization (e.g., hardware acceleration). However, software emulation provides good platform coverage because no specific knowledge of the hardware device is required.

The next advancement in tier 3 I/O virtualization was device paravirtualization. Device paravirtualization employs a split-driver architecture by providing a front-end driver in the guest OS and a back-end driver in the hypervisor or host. The back-end driver, also referred to as a VMM driver interface, works with the native device driver of the host or hypervisor. Paravirtualized drivers can be generic (e.g., class drivers such as network, block drivers) or device-specific. When paravirtualized drivers have device-specific intelligence, they permit guest OS'es to exploit hardware acceleration available in the actual hardware device. Thus, paravirtualization enables concurrent access to a hardware device yet providing close to native performance. To achieve best performance, device-specific paravirtualization requires each device manufacturer to write paravirtualized split-drivers for each device/OS/hypervisor combination. Due to the requirements for paravirtualized split-drivers and prohibitive development and sustenance costs, manufacturers slowly distanced away from device paravirtualization as a solution for software device virtualization. However, because hardware device virtualization (e.g., SR-IOV) drivers require guest-host collaboration with high amount of device-specific intelligence to perform operations such as coordinating power management of devices, split-drivers of paravirtualization still remains a viable solution for I/O virtualization.

The next advancement in tier 3 I/O virtualization was direct device assignment. INTEL and AMD added hardware support for device virtualization. INTEL® VT for directed I/O (VT-d) and AMD's I/O memory management unit (IOMMU) allow a single guest OS instance to exclusively own a device (e.g., a GPU, a storage device, a NIC) while none of the other guests or even the host would be able to use the device while the device is in use. The guest OS may use a native device driver to control the device while VT-d and IOMMU took care of performance issues in software device virtualization such as DMA redirection and interrupt redirection. This allows for a single guest OS to achieve close to native performance for the device, but the exclusive ownership of the device hindered the acceptance of the direct device assignment by the virtualization community. For this reason, direct device assignment is also referred to as a "fixed pass through."

VMWARE®-mediated pass through is a specialized case of direct device assignment (or fixed pass through) that exploits internal architecture details of devices. For example, GPUs support multiple independent contexts and mediated pass-through proposes dedicating just a context, or set of contexts, to a virtual machine (VM) rather than the entire GPU. This enables multiplexing but incurs additional costs. The GPU hardware must implement contexts in a way that they can be mapped to different virtual machines with a low overhead and the host/hypervisor must have enough knowledge of the hardware to allocate and manage GPU contexts. In addition, if each context does not appear as a full logical device, the guest device drivers must be able to handle it. Mediated pass-through lacks interposition features beyond basic isolation. A number of tactics using paravirtualization or standardization of a subset of hardware interfaces can potentially unlock these additional interposition features. For example, the publication entitled "TA2644: Networking I/O Virtualization," VMworld 2008 by Howie Xu, et al. contemplated analogous techniques for networking hardware.

PCI-SIG provides single root I/O virtualization (SR-IOV) that allows device manufacturers to create a single physical device that behave like multiple devices. An SR-IOV device has a single physical function (or physical device) controlled by the hypervisor or VMM, and multiple virtual functions (or virtual devices) each of which can be assigned exclusively to a guest OS. In the case of direct device assignment, VT-d or IOMMU assumes the responsibility for DMA and interrupt redirection. SR-IOV provides better concurrency in the use of the device but still restricted by the finite number of virtual functions that could be accommodated on the hardware device. SR-IOV is gradually gaining adoption in the virtualization community although data centers have to go through extensive infrastructure changes to benefit from SR-IOV.

Nokia contemplated tier 3 device virtualization solution using a system call bridge in United States Patent Application No. 2013/0072260 entitled "Method and Apparatus for Facilitating Sharing Device Connections." The system call bridge is built on the assumption that if a guest OS were to remotely make system calls to the host OS (with appropriate translations in the case of heterogeneous OS'es), host devices could be transparently shared on the guest OS'es. This is a process referred to as system call virtualization. However, system call virtualization that remotes only device operations is impractical or undesirable because the process execution, memory management, information and device management, in that case, will be entirely performed by the host OS. Devirtualization was conceived as a special case of a system call bridge where the operations on selected device files alone are remotely called by the host OS. For example, United States Patent Application No. 2013/0204924 entitled "Method and Apparatus for Providing Application Level Transparency via Device Devirtualization" describes devirtualization.

Devirtualization popularized paravirtualization by removing the need for one driver per each of device/OS/hypervisor combinations. By removing device-specific knowledge from a paravirtualized driver, a single pair of generic (i.e., front-end and back-end) drivers can be used to virtualize many types of devices (e.g., GPUs, sensors) while facilitating (1) the concurrent use of the device across guest OS'es, resulting in higher scalability and utilization of the device and (2) hardware acceleration offered by the device to be used by guest OS'es, resulting in close to native performance. Devices such as GPUs or sensors that do not require a fast response without high volumes of asynchronous operations or DMA/interrupts greatly benefit from devirtualization. Since the devirtualization drivers are devoid of knowledge of any specific devices, the guest OS is required to redirect the virtual file system (VFS) operations for the devirtualized devices (e.g., Linux file_operations) to the devirtualization client driver that works in tandem with the devirtualization host driver on the virtualization host to operate on host devices through the host native device drivers.

Devirtualization virtualizes devices in shared memory domains (e.g., single computers) as well as distributed memory domains (e.g., across a network of computers). For shared memory domains, devices are shared between guest OS'es running on a hypervisor on a shared memory system, thus it is an intrinsic devirtualization. On the other hand, for distributed memory domains, devices are shared between multiple discrete computers (e.g., between a smartphone and a tablet), thus it is an extrinsic devirtualization. Devirtualization has its own limitations, but most importantly devirtualization fails to provide coherent user space device interfaces (e.g., entries in Linux /dev, /sys, /proc filesystems) because the device-specific knowledge out of these drivers was abstracted in favor of genericity of device virtualization. A technical report entitled "Making I/O Virtualization Easy with Device Files" by Ardalan Amiri Sani, et al., Technical Report 2013 Apr. 13, Rice University, April 2013. describes the limitations of devirtualization.

System virtualization infrastructures (e.g., XEN®, KVM, VMWARE® VMI) provided the efficient communication mechanism for a guest OS to context switch into the host. These are similar to system calls that allow applications context switch into the kernel. Context switches can be achieved by software interrupts or VMCALL. Software Interrupts are similar to the system calls and switch to the appropriate ring level to gain the privilege to perform host operations. INTEL® VT provides the VMCALL instruction for a guest to perform an immediate context switch to the host. In VMCALL instruction, one of the arguments indicates a special function that the guest wants the host to perform on its behalf, and the rest of the arguments are operation-specific.

Address space virtualization achieved a significant performance gain for an intrinsic devirtualization. Address space virtualization provides a hybrid address space (HAS) that includes a single address space for the host kernel and guest user mappings while performing devirtualized system call operations in the host and allowing the host kernel to directly access system call arguments (and other information) via virtual address pointers in the guest user application's memory space.

The use of HAS allows enhanced page sharing across OS domains in hypervisor-based system virtualization. Prior examples of page sharing architecture include, but not limited to, XEN® grant tables and VMWARE® transparent page sharing (TPS). For XEN® grant tables, selected memory mappings are shared across guest OS domains (sometimes with the host) to avoid redundant copies of data dealt by device drivers. For VMWARE® transparent page sharing (TPS), when multiple guest OS instances of the same OS function simultaneously, a large number of pages remain identical. The hypervisor shares the backing physical (copy-on-write) pages in the virtual address space of the different guest OS instances. HAS-based page sharing enables a host kernel to directly access any portions of the guest application memory.

The performance of devices such as GPU, storage and NIC usually limits the user experience on a computer system whether it is a physical computer or a virtual computer running on a hypervisor. Operating systems such as Windows, Linux, MacOS, iOS and Android provide native device drivers as closed-source or binary distributions. Some device manufacturers make available an open-source version of their drivers, but they usually withhold many of intellectual property of their drivers. An efficient software device virtualization architecture works seamlessly and transparently across multiple devices, even when only binary level closed-source drivers are available. In such a case, the software device virtualization architecture particularly precludes any specific knowledge about the devices, or access to sources for the devices drivers to be able to efficiently perform software device virtualization.

Dynamic device virtualization (DDV) aims at enhancing I/O performance of application programs running on virtual machines. DDV uses dynamically generated (e.g., cloned) device-specific virtual device drivers for virtual machines (guest processes/threads) based on observing the execution of the host native drivers. In addition, DDV performs zero-copy (direct) I/O in the execution context of the guest processes/threads, by directly accessing the guest user memory from the host kernel based on various address space virtualization techniques (e.g., hybrid address space, kernel address space partitioning, dynamic translation).

DDV is a software device virtualization technique that allows multiple guest operating systems (OS) to concurrently access hardware devices of a computer such as graphics processing units (GPU), storage, network interface card (NIC). Software device virtualization enhances scalability and utilization of hardware devices without requiring special hardware optimization (e.g., single root I/O virtualization (SR-IOV) from PCI special interest group (SIG)). A device manager of DDV running on a supervisory software layer observes a behavior of a native device driver of a hardware device loaded on the host, and clones one or more virtual device drivers to run in the guest OS context. The virtual device driver directly invokes device driver interface (DDI) interfaces (callbacks) implemented by the native device driver, and performs the device management chores on the host that was originally meant to be performed only by the native device driver. Thus, the native device driver is virtually shared between the host and the guest OS domains. The execution context of the native device driver on the host is virtually extended into each of the guest OS contexts. Although DDV provides transparency between host devices and guest applications, virtual device drivers must be dynamically cloned for each guest operation systems and guest applications.

SUMMARY

A system and method for providing dynamic I/O virtualization is herein disclosed. According to one embodiment, a device capable of performing hypervisor-agnostic and device-agnostic I/O virtualization includes a host computer interface, memory, I/O devices (GPU, disk, NIC), and efficient communication mechanisms for virtual machines to communicate their intention to perform I/O operations on the device. According to one embodiment, the communication mechanism may use shared memory. According to some embodiments, the device may be implemented purely in hardware, in software, or using a combination of hardware and software. According to some embodiments, the device may share its memory with guest processes to perform optimizations including but not limited to a shared page cache and a shared heap.

According to one embodiment, the computer-implemented method includes providing a device model for I/O virtualization. The above and other preferred features, including various novel details of implementation and combination of elements, will now be more particularly described with reference to the accompanying drawings and pointed out in the claims. It will be understood that the particular methods and circuits described herein are shown by way of illustration only and not as limitations. As will be understood by those skilled in the art, the principles and features described herein may be employed in various and numerous embodiments without departing from the scope of the present disclosure.

BRIEF DESCRIPTION OF THE DRAWINGS

The accompanying figures, which are included as part of the present specification, illustrate the various embodiments of the presently disclosed system and method and together with the general description given above and the detailed description of the embodiments given below serve to explain and teach the principles of the present system and method.

Figure 1:
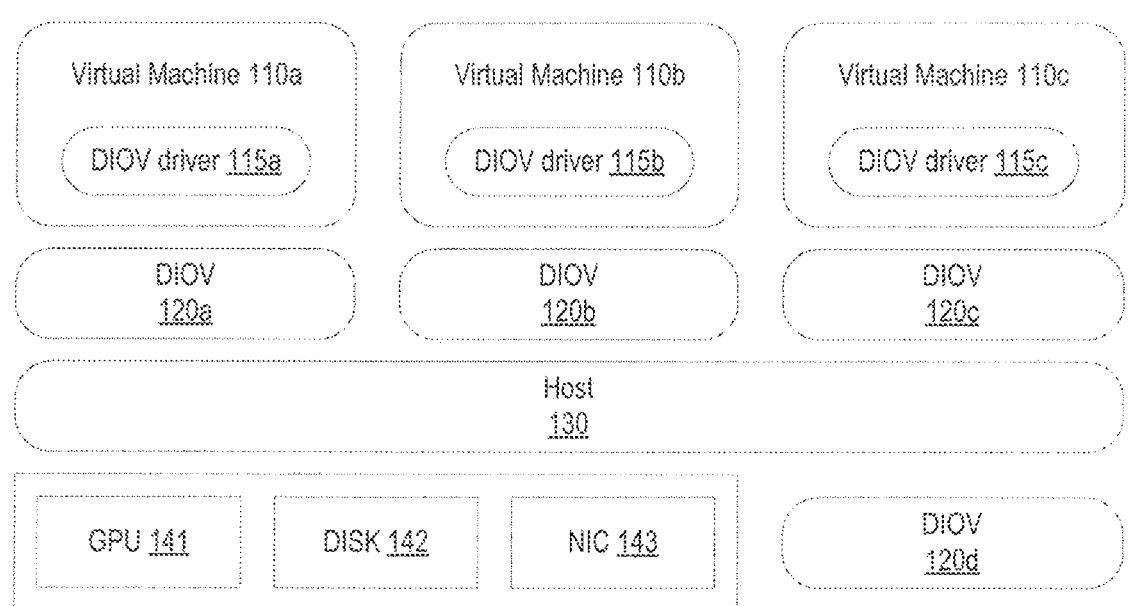
FIG. 1 illustrates an exemplary architecture of DIOV, according to one embodiment.

The figures are not necessarily drawn to scale and elements of similar structures or functions are generally represented by like reference numerals for illustrative purposes throughout the figures. The figures are only intended to facilitate the description of the various embodiments described herein. The figures do not describe every aspect of the teachings disclosed herein and do not limit the scope of the claims.

DETAILED DESCRIPTION

The present disclosure describes dynamic input/output (I/O) virtualization (DIOV) of the computer system. According to one embodiment, a device capable of performing hypervisor-agnostic and device-agnostic I/O virtualization includes a host computer interface, memory, I/O devices (GPU, disk, NIC), and efficient communication mechanisms for virtual machines to communicate their intention to perform I/O operations on the device. According to one embodiment, the communication mechanism may use shared memory. According to some embodiments, the device may be implemented purely in hardware, in software, or using a combination of hardware and software. According to some embodiments, the device may share its memory with guest processes to perform optimizations including but not limited to a shared page cache and a shared heap.

Each of the features and teachings disclosed herein can be utilized separately or in conjunction with other features and teachings to provide a system and method for combining past user events with real-time user events to rapidly respond to advertising opportunities. Representative examples utilizing many of these additional features and teachings, both separately and in combination are described in further detail with reference to the attached figures. This detailed description is merely intended to teach a person of skill in the art further details for practicing aspects of the present teachings and is not intended to limit the scope of the claims. Therefore, combinations of features disclosed above in the detailed description may not be necessary to practice the teachings in the broadest sense, and are instead taught merely to describe particularly representative examples of the present teachings.

In the description below, for purposes of explanation only, specific nomenclature is set forth to provide a thorough understanding of the present disclosure. However, it will be apparent to one skilled in the art that these specific details are not required to practice the teachings of the present disclosure.

Some portions of the detailed descriptions herein are presented in terms of processes and symbolic representations of operations on data bits within a computer memory. These process descriptions and representations are the means used by those skilled in the data processing arts to most effectively convey the substance of their work to others skilled in the art. A process is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like. The steps are not intended to be performed in a specific sequential manner unless specifically designated as such.

It should be borne in mind, however, that all of these and similar terms are to be associated with the appropriate physical quantities and are merely convenient labels applied to these quantities. Unless specifically stated otherwise as apparent from the below discussion, it is appreciated that throughout the description, discussions utilizing terms such as "processing," "computing," "calculating," "determining," "displaying," or the like, refer to the action and processes of a computer system, or a similar electronic computing device, that manipulates and transforms data represented as physical (electronic) quantities within the computer system's registers and memories into other data similarly represented as physical quantities within the computer system memories or registers or other such information storage, transmission or display devices.

The present disclosure also relates to an apparatus for performing the operations herein. This apparatus may be specially constructed for the required purposes, or it may comprise a general purpose computer selectively activated or reconfigured by a computer program stored in the computer. Such a computer program may be stored in a computer readable storage medium, such as, but is not limited to, any type of disk, including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The methods or processes presented herein are not inherently related to any particular computer or other apparatus. Various general purpose systems, computer servers, or personal computers may be used with programs in accordance with the teachings herein, or it may prove convenient to construct a more specialized apparatus to perform the method steps. The structure for a variety of these systems will appear from the description below. It will be appreciated that a variety of programming languages may be used to implement the teachings of the disclosure as described herein.

Moreover, the various features of the representative examples and the dependent claims may be combined in ways that are not specifically and explicitly enumerated in order to provide additional useful embodiments of the present teachings. It is also expressly noted that all value ranges or indications of groups of entities disclose every possible intermediate value or intermediate entity for the purpose of original disclosure. It is also expressly noted that the dimensions and the shapes of the components shown in the figures are designed to help to understand how the present teachings are practiced, but not intended to limit the dimensions and the shapes shown in the examples.

The present system and method provides dynamic input/output (I/O) virtualization (DIOV). DIOV provides several architectural enhancements over dynamic device virtualization (DDV). DDV enhances I/O performance of an application program that is running on a virtual machine using a dynamically generated (e.g., cloned) device-specific virtual device driver for the virtual machine (guest process/thread)

based on observing the execution of the host native driver. DDV performs zero-copy (direct) I/O in the execution context of the guest process/thread, by directly accessing the guest user memory from the host kernel using address space virtualization techniques (e.g., hybrid address space, kernel address space partitioning, dynamic translation).

DDV is a software "device virtualization" technique, whereby devices (e.g., graphics processing units (GPU), storage, network interface card (NIC)) are concurrently accessed from multiple guest operating systems (OS), with full hardware accelerations supported by a native driver of a hardware device of a computer system. DDV enhances scalability and utilization of device hardware without requiring special hardware optimization (e.g., single root I/O virtualization (SR-IOV) from PCI special interest group (SIG)). A device manager of DDV runs on a supervisory software layer, observes the behavior of a native device driver loaded on the host, and dynamically clones virtual device drivers to run in the guest OS context. The virtual device drivers directly invoke device driver interface (DDI) interface (callbacks) implemented by the native device driver, and performs the device management chores on the host that was originally meant to be performed only by the native device driver. Thus, the native device driver is virtually shared between the host and the guest OS domains. The execution context of the native device driver on the host is virtually extended into each of the guest OS context. DIOV enables the transparency of host devices to guest applications but does not require dynamically cloned virtual device drivers.

The present system and method presents a device model for I/O virtualization herein referred to as dynamic I/O virtualization (DIOV). DIOV defines an architecture of a device (herein referred to as a DIOV device) that performs input/output (I/O) virtualization that is agnostic of a hypervisor or a host operating system. DIOV provides efficient virtualization of I/O operations even in a guest process/thread that is running on an alien hypervisor. DIOV device may be embodied as a hardware device (e.g., a SR-IOV PCIe card), a software emulation in a hypervisor, or a hybrid hardware/software implementation. DIOV generically virtualizes I/O operations in a device agnostic manner by abstracting storage as a file system, networking as a protocol, and graphics as a direct rendering manager (DRM). According to some embodiments, DIOV maintains a coherent pool of a distributed shared memory across multiple DIOV hosts. While DDV aims at virtualizing each hardware device, DIOV elevates I/O virtualization to higher abstractions: direct rendering manager (DRM) instead of GPUs, file systems instead of storage devices (e.g., hard disks, network attached storage), and network protocols instead of NICs. DIOV can be implemented in multiple ways, for example, in the hardware (e.g., a PCIe card)), software (e.g., emulation in hypervisor), or a combination of hardware and software components.

Classical virtualization approaches mimic the behavior of I/O devices verbatim, for example, by creating virtual block devices and virtual network interfaces. Unlike classical virtualization techniques, DIOV takes an "intent-aware" virtualization approach. DIOV provides intelligence to determine the intent of a user or an application, and brings about the same effect transparently.

In one embodiment, the present system and method provides storage virtualization via DIOV. The general framework for storage virtualization is applicable to other types of I/O virtualization such as graphics and network. It is apparent that architectural extensions for DIOV to support graphics and networking virtualization can be expounded without deviating from the scope of the present system and method.

According to one embodiment, DIOV is a device herein referred to as DIOV device (DD). It may be implemented as a peripheral component interconnect (PCI) express (PCIe) device, or using a combination of hardware and software components, or fully emulated in software, for example, in a hypervisor. DIOV device is hypervisor agnostic, and delivers portable I/O virtualization across various virtualization software products in the market. For example, a DIOV device that is implemented as a PCIe device can be plugged into a server running virtualization hosts such as VMWARE ESX Hypervisor, CITRIX XenServer, or MICROSOFT Hyper-V. Virtual machines (VMs) running on such a virtualization host benefit from the performance enhancements of DIOV without the knowledge or co-operation of the hypervisor. A DIOV driver presents itself to a guest OS as a combination of: (a) a process and memory manager (PMM), (b) a file system driver, (c) a network protocol driver, and (d) a DRM driver. The forthcoming discussions primarily pertain to the implementation of DIOV device as a software emulation in a hypervisor. However, the general concepts and principles can directly apply to other implementations of the DIOV device such as a PCI Express card, or a hybrid hardware/software implementation. Some optimizations such as the ability to share guest application memory with a host computer via the Extended Hybrid Address Space may be available only in shared memory implementations of DIOV device, when the DIOV device is emulated in the software inside the hypervisor, or when the DIOV device is implemented as a hybrid hardware/software solution.

PMM functions as a process manager as well as an integrated memory manager that spans across the hypervisor, the host operating system, and the guest OS'es. PMM pre-allocates and manages a large chunk of physical memory on the system, and hides this allocated physical memory from the memory manager of the hypervisor and host operating system and makes this physical memory available for DIOV memory optimizations. PMM also manages a large coherent distributed DIOV memory pool across multiple physical computers and forms the basis for cross-domain memory optimizations. PMM formats and initializes the DIOV device for memory optimizations, and integrates the DIOV memory into the address space of each guest (and host) processes enabling them to directly benefit from DIOV memory optimizations without further support from an operating system kernel or the hypervisor.

PMM extends the DIOV memory optimization across different physical computers. Resultantly, the DIOV memory becomes a single logical entity that spans across multiple physical computers. PMM manages the coherency of the DIOV memory across different physical computers. The distributed DIOV memory architecture reduces network operations to memory copies.

According to one embodiment, the present system and method employs an efficient mechanism to execute remote system calls through the synchronized management of the execution contexts of the guest and the host through the deployment of a new management infrastructure referred to as dynamic execution context (DEC). The DEC embodies dynamic components involved when a guest application attempts to perform an I/O operation (remote system call) on the host computer. The actual embodiment of a DEC depends on the mechanism by which the guest and the host communicate to perform an I/O operation, whether they use a blocking hypercall, or whether the guest continues executing past an I/O operation relying on the host to interrupt it when it finishes its I/O operation. DIOV DEC facilitates many advanced optimizations like the ability of host kernel threads performing the remote I/O operations to directly access guest user memory through the memory maps in the Extended Hybrid Address Space (EHAS), and the ability of the host kernel threads to arbitrate page faults occurring while access guest user memory to be resolved by the guest operating systems. In this illustration, we discuss an embodiment of DEC that facilitates an efficient split-context, polling based, asynchronous remote system call architecture using shared memory communication infrastructure herein referred to as streams. However, the general capabilities of DIOV DEC and optimizations they offer will work generically across all remote system call architectures including, but not limited to, the hypercalls implemented via hardware virtualization architectures like INTEL VT and AMD-V. PMM manages the dynamic execution context and enables a guest application to efficiently perform remote I/O operations on the host. In addition, PMM manages the DIOV API for guest (and host) applications to directly avail of DIOV memory optimization services. Even outside the purview of dynamic I/O virtualization, DIOV can be built into a standalone operating system, allowing native computers to benefit from memory optimizations built on local or distributed DIOV memory architecture.

For DIOV memory optimizations, PMM integrates the DIOV memory directly into an address space of the guest (and host) applications. The guest (and host) applications can directly access the integrated DIOV memory without any interventions from a hypervisor or a guest (or host) operating system kernel.

According to one embodiment, the present system and method implements shared memory based storage cache architecture (e.g., a file cache). The DIOV storage cache can be shared across multiple VMs. A single open copy of a file is visible to the processes that are running in the VMs, thereby enabling multiple processes across multiple VMs to read, write, and modify the same file concurrently and coherently. Coherency is enforced by the shared memory architecture of the computer system.

According to another embodiment, the present system and method provides a shared heap that is shared by applications on multiple guest (and host) operating systems. These applications can dynamically allocate memory for their use. For example, a guest process may call a DIOV API to dynamically allocate a memory chunk of 64 GB by making a call to the DIOV memory allocation (diovmalloc) function without the knowledge of the guest OS:

$$char * diovmen = (char^*)diovmalloc(64 * GB);$$

Generalizing DIOV memory optimization, DIOV API can enable third party vendors to write their own memory optimizations. For example, a vendor can implement a coherent network cache using the DIOV PMM framework.

According to one embodiment, the DIOV storage architecture exports a host directory as a "DIOV storage device" that can be mounted on a virtual machine. The mount of the host directory on the VM provides the flexibility of network file system (NFS) and allows for an efficient sharing of a DIOV storage device across multiple VMs. In this sense, the DIOV storage may be referred to as an "NFS over shared memory" because it does not incur the network overheads of a conventional NFS.

FIG. 1 illustrates an exemplary architecture of DIOV, according to one embodiment. A host 130 (a hypervisor) runs one or more guest OS'es, each in a virtual machine (110a-110c). The DIOV device 120d is implemented in hardware (e.g., a PCIe card), in software (e.g., emulated in a hypervisor), or with a combination of hardware/software components. Logically, the DIOV device 120d is presented to the hypervisor (or the host operating system) as a SR-IOV capable PCI express device. The virtual functions of this SR-IOV device (120a-120c) are presented to the guest OS'es as DIOV virtual devices. The guest OS loads the DIOV device driver (115a-115c). The host 130 has a GPU 141, a disk (or storage device) 142, and a network interface card 143. The DIOV device driver 120 functions as a combination of a process and memory manager (PMM), a DRM driver (for graphics), a file system driver (for storage), and a network protocol driver (for networking). It is apparent that other peripherals or hardware devices may be installed on the host 130, and the DIOV device driver can support such peripherals or hardware devices without deviating from the scope of the present disclosure.

In classical virtualization, virtual machines are isolated via hardware abstraction layer. The isolation of virtual machines adds software emulation overheads and hides device hardware capabilities from the virtual machines. The virtual machines do not know about a device's capability of hardware acceleration, thus cannot benefit from it. Examples of such hardware acceleration capabilities include, but are not limited to, TCP-IP/CRC offloads for NICs and 3D acceleration for GPUs. The present system and method makes I/O virtualization more efficient by removing the hardware abstraction such that guest applications in a virtual machine can see and share devices while honoring isolation. The guest applications can query the virtual file system on the host through the DIOV interfaces to identify what hardware acceleration features are supported by the host devices and offload those capabilities to the host devices efficiently. The DIOV framework also provides a high level of security because the DIOV memory is visible only to DIOV drivers and the access to the DIOV memory is gated through the use of the Extended Hybrid Address Space (EHAS). The DIOV framework employs a device model for providing generic I/O virtualization.

Dynamic Execution Context (DEC)

When a process makes a system call to perform an I/O operation, the process makes a context switch from the user space to the kernel space and executes codes that are necessary to write data in the application's memory space into the appropriate device, or to read from the device into the application's memory space. The components involved in executing a system call (e.g., a code executing in the user application, a system call interface in the kernel, a kernel code that performs the device operation, arguments passed to the system call) are referred to as an execution context. The execution context describes the architectural state of an application process throughout the execution of a system call, including values in the registers, values on the user/ kernel stack, values in virtual memory, and the mechanisms for the virtual address translation (e.g., page-tables), etc. Similarly, when an application or a kernel executes a hypercall into a hypervisor, the execution context spans the application process code, the guest operating system code, the hypervisor code, and the mechanisms for transferring values back and forth through the hypercall (e.g., register values, values in stack and guest virtual memory).

In order for a guest application to perform an I/O operation on a host device, devirtualization and DDV perform frequent interrupt-driven context switches from the guest application to the host operating system (and back) through hypercalls. This single context execution of the context switches is disruptive for the guest process/thread (that has to wait for the operation to complete) and for the host (that is interrupted for each I/O operation). The single execution context in the case of DDV includes a transition from guest threads to the guest kernel space, and from the guest kernel space to the host kernel when it executes a native device driver code to perform an appropriate I/O function on the device and returns control back to the guest application.

The present system and method uses a split-context, cross-domain, polling based, remote asynchronous system call (e.g., virtual file system operations) mechanism called "streams".

The present system and method employs a shared memory mailbox referred to as a stream for asynchronous execution of system calls. A stream has a header, a set of descriptors for remote system call operations (herein referred to as ops) together with their arguments, and a finite state machine (FSM) that monitors the progress of each operation. A guest operating system allocates a set of streams from the DIOV memory. The streams may be configured in multiple ways, for example, per-process, per-thread, per-file-or-socket-descriptor, or system (domain) wide. Once allocated, the streams are registered with the host. The host assigns each stream to a kernel thread to start polling for guest-generated system call requests. There may be one kernel thread per stream, or each kernel thread may be polling multiple streams depending on the configuration. When a guest thread generates requests for a system call to be performed on the host, it allocates a stream op from its designated stream and writes the requests onto the stream op. The host polls the streams and the ops therein for I/O requests and dispatches the requests at its own pace. In the meantime, the guest threads may execute past the current system calls operations and generate more requests, or simply wait for the queued system calls to complete. The guest threads need to poll its stream ops for completion of I/O requests that they originate.

DIOV system calls complete across a split-context, i.e., a guest thread that generates a system call request, and the host kernel thread that dispatches and completes the system call request. DIOV ensures the information (e.g., arguments) needed by the host kernel to perform a system call is passed through streams. Register values are passed through stream ops argument slots. If a stack is not visible through virtual memory mapping, relevant stack variables are passed through stream ops argument slots (for example, in Linux, stacks for threads are visible globally). Pointers to the guest user memory are passed through stream ops argument slots. In the case of software emulation of a DIOV device in a hypervisor, and in hybrid hardware/software implementations of the DIOV device, the Extended hybrid address space (EHAS) ensures that the guest user memory is accessible from the host kernel to perform the system call.

The guest OS maintains a DIOV guest context (DGC) descriptor, and the host OS maintains a DIOV host context (DHC) descriptor. Both the DGC descriptor and the DHC descriptor are keyed by a global DIOV context ID to ensure that the host executes the system call in the EHAS corresponding to the guest process/thread that originate the system call. The DGC contains the information needed to accurately translate a guest process's virtual address. Before a guest thread generates a system call request, the guest thread makes sure that none of the memory management parameters has changed. In the case of INTEL processors, a guest thread checks if the memory management modes defined by CR0/CR4 has not changed, if the values of segment descriptors (i.e., LDT/GDT entries) corresponding to the appropriate segment selector (usually data segment (DS)) and the root page table have not changed. If they are changed, the translations cached in EHAS are invalidated.

The simplified pseudo-code for a lifecycle of DIOV is as follows:

context ID of the originating guest process. For a simple operation, the dynamic execution context for a remote system call includes a guest thread, a stream for I/O, a kernel thread of the host that polls the stream, and a DIOV host context (DHC) and an extended hybrid address space (EHAS). For a remote system call operation resulting in a page fault on the host, the host DIOV driver communicates with the MMA on the guest to handle the page fault and hand over the page mappings needed by the host to fix the EHAS mapping. In this case, the dynamic execution context additionally spans the guest MMA, the DIOV guest context

TABLE 1

| pseudo-code for a lifecycle of DIOV remote system call execution | |
| --- | --- |
| Guest Operations | Host Operations |
| | Hypervisor boots. |
| | Hypervisor - PMM pre-allocates memory |
| | for DIOV optimizations. |
| | Host starts up. |
| | Host PMM queries hypervisor about |
| | DIOV Device |
| | Formats DIOV Device |
| |    Initializes Streams |
| |    Initializes Storage Cache |
| |    Initializes Shared Heap |
| |    Initializes other memory |
| |     optimizations |
| | Maps DIOV Device into Host memory |
| Guest boots. | |
| Guest queries hypervisor for DIOV | |
| Device configuration. | |
| Creates Master Map for DIOV Device. | |
| Guest process requires to perform remote | |
| I/O. | |
| Maps Master Map for DIOV Device into | |
| process. | |
| DC = f(domain, process); | |
| If first request: | |
|    Allocate and initialize DGC[DC] | |
| stream = get_stream(DC); //Alloc if first | PMM request to bind a host context. |
| req | If first request: |
| stream->context = DC; |    DC = stream->context; |
| Invoke PMM to bind a host context for |    Allocate and initialize DHC[DC] |
| this process. |    Allocate a kernel thread |
| | Assign stream to an appropriate kernel |
| | thread. |
| ops = <empty>; | for each op in stream |
| for each operation to perform | do |
| do |    use_mm(DHC[DC]->ehas_mm); |
|    op = get_op(stream); |    op->result = perform_syscall(op); |
|    op->op = read; |    unuse_mm(DHC[DC]-> |
|    op->args[0] = fd; |    ehas_mm); |
|    op->args[1] = ...; |    op->state = completed; |
|    op->state = initiated; | done |
|    ops.add(op); | |
| done; | |
| for each op in ops | |
| do | |
|    if (op->state != completed) | |
|     Do something else; | |
| done; | |

Dynamic execution context (DEC) includes various components that allow guest processes/threads to perform remote system calls using the DIOV framework. Examples of such components include, but are not limited to: a guest process/thread, a DIOV guest context (DGC), a remote system call interface to the host kernel, a host kernel driver for DIOV, a DIOV host context (DHC), and a guest memory management agent (MMA). Each guest process has a context ID computed as a function of (domain, process_id). Each remote system call operation identifies itself with the (DGC), and a stream used for communication between the host DIOV driver and the guest MMA.

Figure 2:
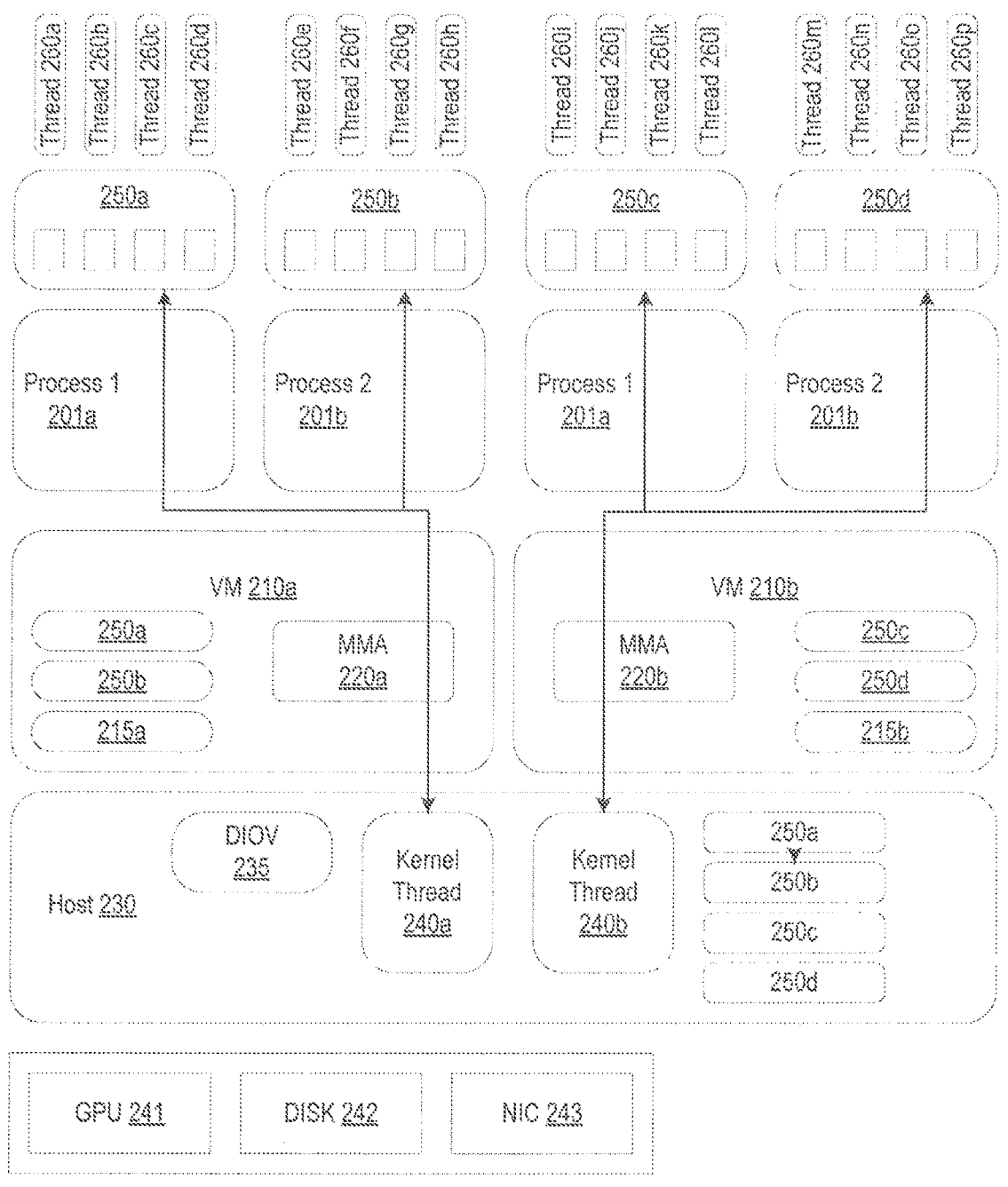
FIG. 2 illustrates an exemplary dynamic execution context, according to one embodiment.

The present system and method provides a split-context, polling based, remote system call interface called "streams". Streams enable a shared memory, inter-domain communication between a host kernel and a guest thread. An I/O operation initiated by a guest thread writes a request to a stream. The guest thread monitors the finite state machine of the stream until the requested I/O operation completes. FIG. 2 illustrates an exemplary dynamic execution context, according to one embodiment. The host computer 230 has one or more I/O devices connected to it—most notably a GPU 241, a hard disk 242, and a NIC 243. When the host 230 boots up, it loads the DIOV host driver 235, initializes streams 250*a*-250*d*, and assigns kernel threads 240*a*-240*b* to poll the streams 250*a*-250*d*. The number of streams and the number of kernel threads can be arbitrarily large, and there can be a many-to-many relationship between them as well. The virtual machines 210*a*-210*b* boot up, and they load the DIOV virtual drivers 215*a*-215*b*. There can be an arbitrary number of virtual machines. The DIOV virtual drivers 215*a*-215*b* communicate with the host (through one of many mechanisms including hypercalls) to allocate their share of streams 250*a*-250*d*. The guest OS'es in the virtual machines 210*a*-210*b* then start different processes 201*a*-201*b*. Each guest process 201*a*-201*b*, when trying to make a remote system call for the first time, consults the DIOV virtual driver 215*a*-215*b* and allocates a stream for itself. Each guest thread 260*a*-260*p* of the guest processes 201*a*-201*b*, when trying to perform a remote system call, allocates a stream op in the streams 250*a*-250*d*. The guest thread writes the arguments to the remote system call in the current stream op and writes a bit to indicate that the stream op is ready to be deployed on the host (hypervisor or host operating system) 230. The kernel thread 240*a*-240*b* that polls for this stream sees this bit set in the stream op and dispatches the operation to be performed in the host kernel. Once the operation completes the kernel thread 240*a*-240*b* writes the results into the stream op and sets another bit in the stream op that the finite state machine in the guest thread 260*a*-260*p* is polling for. The guest thread 260*a*-260*p* sees the operation is complete, and continues its execution. During the executing of the operation in the host kernel, the host kernel driver may encounter page faults while accessing guest user memory due to missing mappings in the EHAS. A page fault handler in the host kernel recognizes a page fault happened in a particular guest process 210*a*-210*b*, and works with the MMA 220*a*-220*b* of the guest 210*a*-210*b* to (a) resolve the page fault in the guest 210*a*-210*b*, and (b) return the page mappings so that the DIOV host driver 235 can fix the EHAS for the appropriate kernel thread 240*a*-240*b* so that the operation can continue on the host.

Examples of the content of the DIOV guest context descriptor and the host context descriptor include, but are not limited to, the followings:

TABLE 2

| guest context descriptor and host context descriptor | |
| --- | --- |
| DIOV Guest Context Descriptor | DIOV Host Context Descriptor |
| Context ID = f(domain, process) | Context ID = f(domain, process) |
| DIOV Host Context Descriptor | DIOV Guest Context Descriptor |
| Control Registers (CR0, CR4) | Guest Memory Management |
| Segment Descriptors | Agent to handle page faults |
| corresponding to segment | Host Memory Context (EHAS) |
| selectors: CS, DS, SS, ES, FS, GS | corresponding to the Guest |
| Guest Process's Memory Context | Process (ehas_mm) |
| (mm) | List of Virtual Memory Areas |
| Guest Process's Extended Memory | (VMAs) |
| (EHAS) Context (ehas_mm) | Guest User VMAs |
| List of Virtual Memory Areas | Host User VMAs |
| (VMAs) | VMAs for DIOV Memory |
| Guest User VMAs | Selected portions of Guest |
| Host User VMAs | and Host Kernel Address |
| VMAs for DIOV Memory | Spaces (optional) |
| Optionally: Selected | |
| portions of Guest and Host | |
| Kernel Address Spaces | |

When a page fault occurs during the execution of a remote system call on the host, the DHC's fault handler first determines the DGC of a guest process in which the fault occurred. The fault handler works with a memory management agent (MMA) of the guest process to resolve the fault on the guest process, and invokes a hypercall to map the resulting machine page (MPN) into its memory (i.e., EHAS for the current guest process). This works seamlessly for any type of paging models in a hypervisor such as direct paging (for paravirtualization), shadow paging (for HVM guests), or hardware assisted paging (HAP) (for hardware virtual machine (HVM) guests with support for INTEL's extended page table, or AMD's nested page table). The simplified pseudo-code for the guest memory management agent that resolves a fault looks like the following (in Linux):

```
p = task(guestcontext);
if ((memory management modes haven't changed - in CR0, CR4, etc.) or
    (segment descriptors for the current operation has changed - mostly
    DS))
{
    // Extremely infrequent: Does not happen on Linux guests!
    Invalidate all translations cached so far in the Hybrid Address Space.
}
vma = find_vma(p->mm, faultaddress);
vmf.virtual_address = faultaddress;
if (vma->vm_ops->fault)
    vma->vm_ops->fault(vma, &vmf);
else
{
    page = alloc_page(GFP_USER);
    vm_insert_page(vma, faultaddress, page);
}
```

Extended Hybrid Address Space (EHAS)

The hybrid address space (HAS) is used in devirtualization and DDV. HAS has a single host kernel address space and a single guest user address space, and no information of the finer composition is needed. The use of HAS is unidirectional because only a host kernel uses HAS to directly access a guest user memory when performing a system call on behalf of the guest thread. The guest memory map cached into HAS is always persisted. Therefore, the lack of knowledge of the composition of the address spaces prevents portions of the mapping to be removed when a guest process explicitly unmap a region (e.g., using munmap(2)). EHAS provides enhancements to the hybrid address space (HAS) used in devirtualization and DDV.

Figure 3:
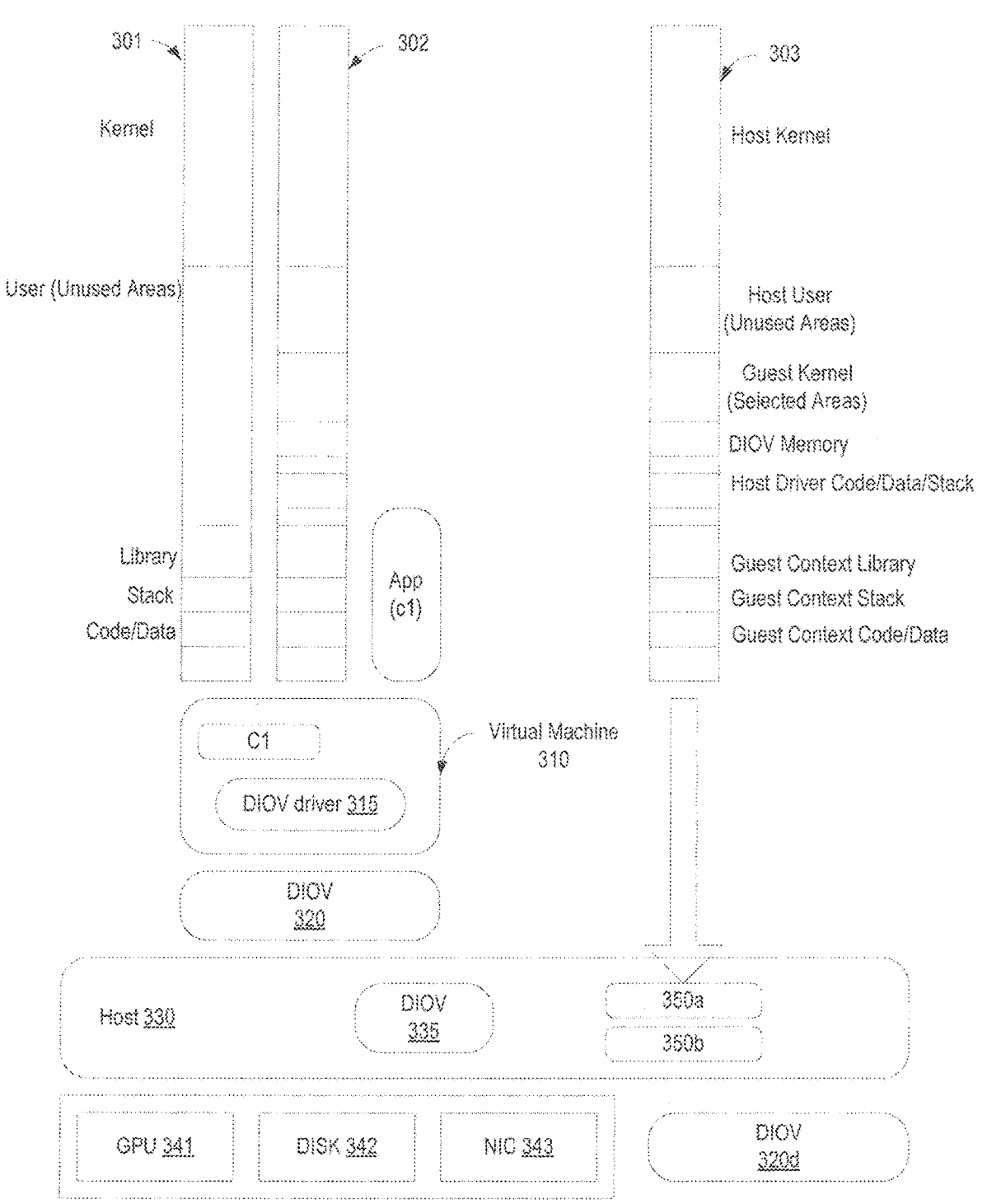
FIG. 3 shows an exemplary schematic diagram for EHAS, according to one embodiment.

FIG. 3 shows an exemplary schematic diagram for EHAS, according to one embodiment. The address space 301 is the original address space (i.e., memory context) of a guest user process including a kernel address space, and a user address space. The user address space comprises the address space used by the guest, library, stack, and code/data components. The EHAS 302 for the guest user process is formed by augmenting the guest address space with information about the mappings of (a) DIOV memory, (b) the code/data/stack for the host DIOV driver, and (c) selected portions of the guest kernel mapped for reference by the host DIOV driver. Typically, for security reasons, the EHAS 302 will be a separate address space (page table) and different from the address space 301 created by the guest OS. However, this involves some performance overheads because the right EHAS needs to be validated and reinstated for the guest OS to successfully execute remote system calls (more details are discussed below). So, the host DIOV driver may choose to merge the EHAS 302 components above into the original address space 301 upon a user's assertion that the process is "well-behaved". The EHAS 303 is the same extended hybrid address space (EHAS) in the DIOV host context of the host DIOV driver.

The extended hybrid address space (EHAS) supports several features that are not available on DDV. The use of EHAS is bidirectional. EHAS is used by a guest process to access the DIOV memory, and by a host to access the memory of the guest process (not only guest user memory, but also selected portion of the guest kernel memory in some cases).

According to one embodiment, EHAS provides tracking of finer components of the virtual address space on both the guest side and the host side. In Linux terms, the virtual memory areas (VMAs) determine a mapping for a region of a virtual memory (identified by a start and end addresses, flags, page fault handler, etc.). For example, the EHAS has the following VMAs (fixed vs. relocatable mappings are explained below):

a. guest user address spaces (fixed mappings)
b. host user address spaces (relocatable mappings)
c. VMAs created for DIOV memory (relocatable mappings)
d. VMAs created in the user address space for selected portions of guest kernel address space (via optimization on block device drivers and network interfaces). (relocatable mappings)

The virtual address space of the host process or the host kernel thread that performs remote system calls on behalf of a guest process is under the control of the DIOV driver 335. The guest process that originates a remote system call is free to use any portion of its allotted user address space. Other VMAs that are mapped into the EHAS by DIOV are moved to make room if the guest process requires to use any portion of its address space. For example, a guest process may want to perform a MAP_FIXED memory mapping (Linux mmap (2)) onto an address range where one of the EHAS VMAs is mapped. This can be dangerous, since the new mapping may silently wipe out the EHAS VMA mapping. To prevent this, for each guest process, a separate memory context (a "struct mm_struct" in Linux terms, or simply said a page table) is maintained for EHAS—onto which the VMAs corresponding to the host user address space, the DIOV memory and relevant portions of the guest kernel memory are mapped. Before each guest DIOV operation (e.g., a remote system call) is initiated, the DIOV driver checks if any changes have been made to the original memory context of the guest process, for example, if a VMA is added or deleted. These changes are reflected into the EHAS both on the host side and on the guest side. It is also conceivable to share the same physical memory page containing EHAS on the guest as well as the host. If a newly added VMA in a guest process overlaps with one of the VMAs that was added by the DIOV driver into EHAS, the latter VMA is relocated to a free slot in the address space, so that the former VMA (i.e., VMA created by the guest) can occupy the address range the user application intended it to have. If a guest operation has to use EHAS (e.g., using DIOV memory for storage cache access or management), the guest operation has to explicitly switch to the EHAS memory context before performing the operation. Frequent switching between the original address space and the EHAS may result in a performance penalty because the translation lookaside buffers (or TLBs) need to be flushed every time the page tables are changed. Upon a user assertion that a guest process is well-behaved and obeys the operating system's discretions on the memory mapping (e.g., does not force a MAP_FIXED mmap operation), the DIOV driver 315 may permit the EHAS VMA to be mapped directly on the original memory context of the guest process to achieve a better runtime performance. This user assertion may be made in a general way if the user who created the guest knows a priori that all processes in the guest are going to be "well-behaved". Otherwise, each guest process may perform a special DIOV I/O control (ioctl) operation to indicate that it is "well-behaved".

According to one embodiment, EHAS supports dynamic synchronization of the guest user VMAs. As discussed above, before each guest operation (e.g., a remote system call) is initiated, the DIOV driver checks whether there has been any change to the guest process's user address space. Any change (e.g., addition, deletion, modification) to the user VMAs in the guest user address space needs to be immediately reflected in the EHAS's of both the host (in the DHC) and the guest (in the DGC) if the EHAS is different from the original context. This ensures that the host kernel does not perform a remote system call with the stale mappings in the EHAS.

According to one embodiment, EHAS provides both fixed and relocatable mappings. Depending on how the target memory is accessed, the EHAS can have fixed mappings or relocatable mappings. The fixed mappings refer to VMAs that have to be mapped at identical virtual addresses and cannot be moved to a different virtual address slot. The relocatable mappings refer to VMAs that can be mapped at any free slot in the EHAS, provided the translation function is known. The mappings of the VMAs of the guest process always have to be fixed mappings. Suppose that a data structure read from one of these VMAs contains a pointer to other memory locations in the same VMA. If this VMA is remapped at a different location, the DIOV driver may be able to read the data structure or fault (or read incorrect values) when trying to dereference the pointer inside the data structure because the VMA has moved and the pointers are referencing the wrong memory locations. According to one embodiment, the mapping of the DIOV memory never contain an internal pointer so that they can be relocated anytime to any free memory slot in the EHAS address space. In INTEL's 32-bit architecture (or in a compatible mode), when segment bases can be non-zero, even the fixed mappings may be relocated by an offset specified in the segment base address of the appropriate segment selector (usually DS). In pure 64-bit mode, only FS and GS have proper segment bases, and the base addresses of all other selectors are considered to be zero.

DIOV Device

The device model for DIOV is an architecture specification that can be implemented exclusively in hardware (e.g., a PCIe card), exclusively in software (e.g., emulated in a hypervisor), or using a combination of hardware/software components. Conceptually, in the hardware implementation as a PCIe card, DIOV device presents itself to a hypervisor (or a host) as a logical single root I/O virtualization (SR-IOV) device that exposes its virtual functions as DIOV virtual devices to various virtual machines running on the host. The DIOV device driver, when loaded by the guest OS, functions as a combination of process and memory manager (PMM), file system driver, network protocol driver, and DRM driver.

According to one embodiment, a DIOV device has a large pool of memory that can be configured to perform memory optimizations. Examples of such optimization include, but are not limited to: (a) a shared storage cache (or page cache) that is shared across VMs, (b) a shared heap that provides a dynamic memory allocation service to guest processes without the knowledge of the guest OS, and (c) third party memory optimizations (e.g., network caching) that can be built using DIOV APIs. The guest applications across multiple VMs can directly access the DIOV memory and operate on a much larger memory space than is known to the respective guest operating systems.

PMM is a process manager and an integrated memory manager spanning across the hypervisor, the host operating system, and the guest operating system. The PMM in the host operating system is responsible for memory management on the host and controls all the system memory. The PMM saves most of the memory to be used by DIOV (DIOV memory), and gives the rest to the host operating system to allocate amongst all its memory consumers. The PMM is responsible for managing a distributed coherent pool of DIOV memory (coherent distributed shared memory) across multiple physical computers. Thus, PMM is at the heart of all DIOV memory optimizations—some of them local to the current host (physical computer) and others cross-domain (across multiple hosts or physical computers).

According to one embodiment, the DIOV driver and the associated DIOV-aware virtual drivers (e.g., file system, socket protocols, and DRM drivers) are implemented as kernel mode drivers that reside in the host and the guest kernels. According to another embodiment, the DIOV driver and the associated DIOV-aware virtual drivers are implemented as user mode drivers that execute in the user mode with kernel hooks for the drivers. According to yet another embodiment, the DIOV driver and the associated DIOV-aware virtual drivers are implemented as user space programs (or services) that communicate to the kernel using standard system calls. For the purpose of simplicity and illustration, the present example refers to the DIOV drivers as kernel mode drivers that operate in the guest and host operating system kernels. However, it is apparent that the other types of DIOV drivers may be contemplated without deviating from the scope of the present disclosure.

In a legacy mode where unmodified guest applications can benefit from DIOV, a guest kernel driver acts as a primary initiator of a DIOV operation (e.g., a remote system call). In a "DIOV API" mode where the user writes new guest applications with DIOV API, the guest applications bypass the guest kernel for performance critical operations (e.g., reads and writes on files), and directly communicate with the host drivers (either in host kernel or host user space) to perform the performance critical operations. In this case, the DIOV API in the guest user space acts as the initiator for the DIOV operations.

Figure 4:
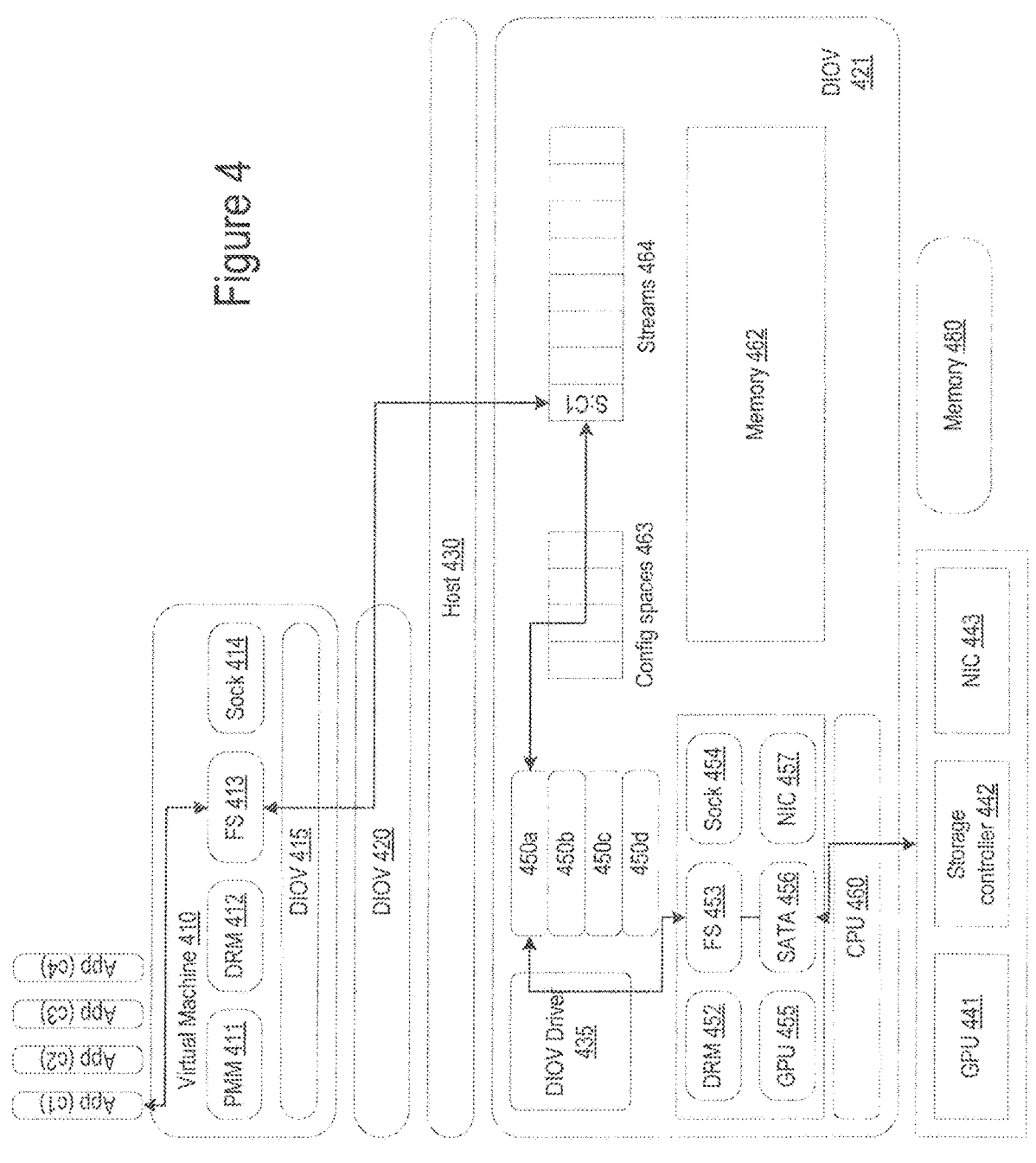
FIG. 4 illustrates an exemplary implementation of a DIOV device, according to one embodiment.

FIG. 4 illustrates an exemplary implementation of a DIOV device, according to one embodiment. A DIOV device 421 is implemented in hardware (e.g., a PCIe card) with multiple master inputs for hardware devices such as GPU 441, storage controller 442, NIC 443, and memory 480. The DIOV device 421 presents itself to a hypervisor (or virtualization host 430) as a SR-IOV device. The host DIOV driver 435 is loaded at a boot time. The hypervisor sees multiple virtual functions of the DIOV device 421 (each presenting as a PCIe configuration space 463). Each of the virtual functions is directly assigned to a VM 410 as the DIOV virtual device 420. The hardware identification (e.g., vendor/device ID in PCIe terminology) of the virtual functions 420 of the DIOV device 421 causes the guest DIOV driver 415 to be loaded. The on-board memory 462 is used for DIOV memory optimizations including, but not limited to, shared storage cache, shared heap, shared network cache, etc.

The process and memory manager (PMM) of the host DIOV driver 435 reads raw device configuration from the hypervisor, formats the DIOV device 421, initializes streams 464, configuration spaces 463, and memory 462 for optimization (e.g., storage caching, shared heap), and creates a master maps for the DIOV device 421 in the host memory (including streams, config spaces, and DIOV memory). The guest DIOV driver 415 reads the DIOV device configuration from the hypervisor, and reads the master map for the DIOV device 421 from the host. The master map for the DIOV device 421 is subsequently mapped into the address spaces of guest processes/applications that perform remote system calls to the DIOV device 421 via streams 464. The DIOV host driver 435 assigns kernel threads to poll streams 464 for incoming requests for remote system calls from guest processes. Once these kernel threads detect a request for remote system call, the kernel threads communicate their intent to perform I/O operations to the DIOV host drivers (e.g., DRM 452, file system 453, socket 454 that works with the native drivers, GPU 455, SATA driver 456, NIC 458) to complete the I/O operations. The process and memory manager (PMM) of the DIOV host driver 435 of the DIOV device 421 is responsible for establishing handshakes between the guest processes and the DIOV device 421 to create the dynamic execution context (DEC) components to enable each guest process to initiate a remote system calls. The PMM driver provides an interface for the guest processes to directly make use of DIOV memory optimization, for example, access and manage the shared storage cache, dynamically allocate memory from the shared heap, etc. The PMM driver also enables a third party vendor to build products or services based on the coherent distributed DIOV memory using the DIOV API.

A "DIOV API" may be implemented in a high-level program language (e.g., C, C++, Java, Perl, Ruby, and Python). The DIOV API enables a guest user application to directly operate on the DIOV infrastructure to perform operations without intervention from the guest kernel. Examples of such operations include, but are not limited to:

Direct communication with host DIOV driver to perform storage, networking, and graphics operations (say, using the stream interface).

Using the enhanced shared memory services such as shared page cache and shared heap (e.g., dynamic memory allocation).

Implementation of third party vendor products (like coherent network cache) on top of DIOV PMM using DIOV API.

Figure 5:
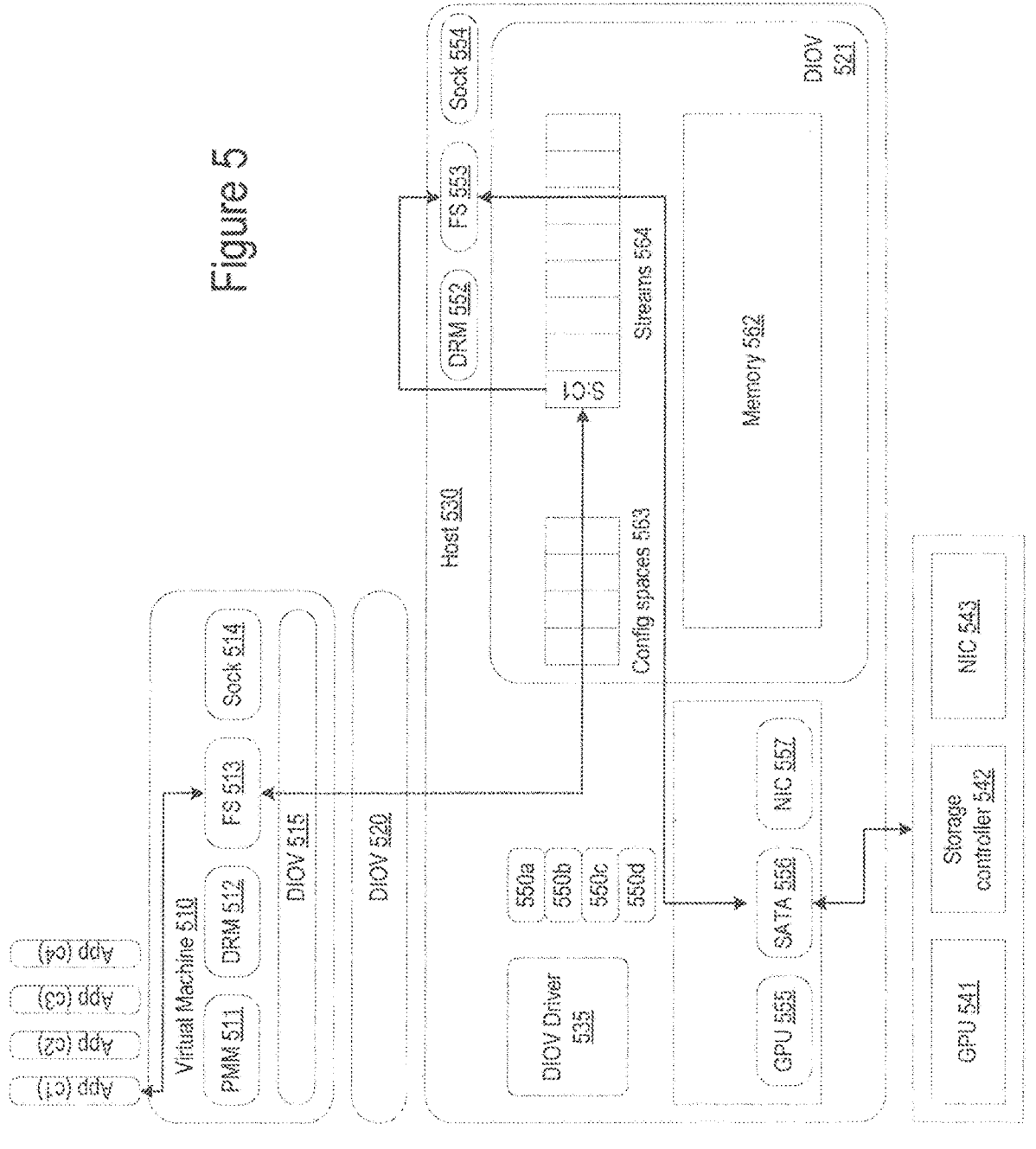
FIG. 5 shows an exemplary DIOV device architecture emulated by software in a hypervisor, according to one embodiment.

FIG. 5 shows an exemplary DIOV device emulated by software in a hypervisor, according to one embodiment. The PMM in the DIOV host driver 535 on the hypervisor 530 (e.g., Xen Hypervisor) or the host operating system 530 controls all the system memory 562, and it sets apart a large pool of memory during the early boot phase for exclusive use by DIOV (DIOV memory), and gives the remaining memory to the hypervisor or host operating system to allocate to its memory consumers. Typical servers have a large amount of memory (e.g., 768 GB, 1 TB of DRAM). A field study by Storage Switzerland, LLC revealed that most often less than half of the server memory is actually used. The present system and method uses a large portion of the memory (e.g., 500 GB) for DIOV optimizations. The PMM keeps track of the hypervisor's or host operating system's memory consumption. When it determines that the hypervisor or the host operating system is running low on allocable memory, the PMM reclaims some of its own memory and gives it to the hypervisor or the host operating system.

The PMM in the host DIOV driver 535 formats the DIOV memory into streams 564, configuration spaces 563, shared storage cache, shared heap, etc. According to one embodiment, the DIOV device emulated in software inside the hypervisor also behaves like a SR-IOV device in such a way that its emulated virtual functions are given to the virtual machines as virtual DIOV devices. The DIOV operation implemented in the hypervisor occurs similar to the DIOV device implemented in the hardware. However, it should be noted that when DIOV device is emulated in software (inside the hypervisor or host operating system) or implemented using hybrid hardware/software components, there is no strict need for the DIOV device to be modelled as a SR-IOV device-it can assume any private interface understood by the host and guest DIOV drivers.

ORACLE's Transcendent Memory (TMEM) allocates a large pool of memory from Xen heap for various optimizations. While TMEM primarily focuses on non-persistent memory pools from Xen heap, in the present system and method, the PMM is the primary memory allocator on the hypervisor or host operating system and it saves a large pool of memory for use by DIOV and releases the rest for management by Xen heap (or the memory manager in the host operating system). The primary difference between TMEM and DIOV is with respect to the manner in which they (a) allocate and (b) use memory. TMEM sits beneath the memory allocator of the hypervisor (like Xen) or the host operating system and allocates and manages pools of memory allocated from the system heap. DIOV's PMM is the primary memory allocator in the hypervisor or the host operating system and it pre-allocates a large chunk of memory for private use by DIOV, and releases the rest of the memory for use by the hypervisor or the host operating system—the hypervisor or host operating system never sees the memory acquired by DIOV PMM. PMM watches the memory consumption of the hypervisor or host operating system and when it falls below a critical level, PMM relinquishes some of its own memory and gives to the hypervisor or host operating system for its own consumption. Guest operating systems request TMEM to allocate pools of memory for various optimizations (like shared page cache in a cluster of VMs), while DIOV Memory remains private to DIOV. The DIOV memory is completely organized and manipulated by the DIOV host driver. The guest PMM driver maps DIOV memory into guest processes as instructed by the DIOV host driver—even the rest of the DIOV drivers (file system, network protocol, or DRM drivers) only sees references to DIOV memory and is not aware of any mechanism to control or manipulate the mappings in the guest user processes.

DIOV Storage Virtualization

Classical virtualization of storage devices provides a virtual block device that can be mounted by a file system (e.g., ntfs, ext4, ufs) on a directory in the guest operating system. DIOV exports a host directory (e.g., a mount point of a storage device) as a "DIOV storage device" to be mounted on a directory in the guest operating system by the DIOV file system. On the host, a block device (e.g., a direct attached storage (DAS) device like a spindle hard disk or a solid-state disk (SSD), or a network-attached storage (NAS) or a NAS device) is mounted on a directory by an appropriate file system driver. The host DIOV driver then "exports" this directory as a "DIOV storage device" that can be mounted by the guests. The DIOV file system driver on the guest mounts this "DIOV storage device" on a directory in the guest. This is akin to the network file system (NFS) where a remote host directory (e.g., a mount point) is mounted as a device. For example, a real file system can be mounted on the host by executing the command: "mount/ dev/sda10/exports/astro." A Typical NFS of this directory on the guest can be mounted by excuting the command: "mount 192.168.0.2:/exports/astro/mnt." The equivalent DIOV mount on the guest is: "mount host:/exports/astro/mnt."

NFS provides concurrent sharing of files from the same device (e.g., DAS or NAS) across multiple computers or domains. DIOV storage provides the flexibility of NFS for sharing files from a device across multiple domains (or virtual machines). In the case of NFS, the communication between the guest and the host for storage access is via a network interface where the overhead is higher due to the network traffic. DIOV storage is advantageous over NFS because the communication between the guest and the host for storage access is via the shared memory (i.e., DIOV streams). In addition, DIOV does not transfer data when the guest requests an I/O operation. Only the virtual addresses of guest user memory are passed to the host DIOV driver, and the host kernel can directly access guest user memory though the virtual addresses of the guest user application mapped in the EHAS.

Figure 7:
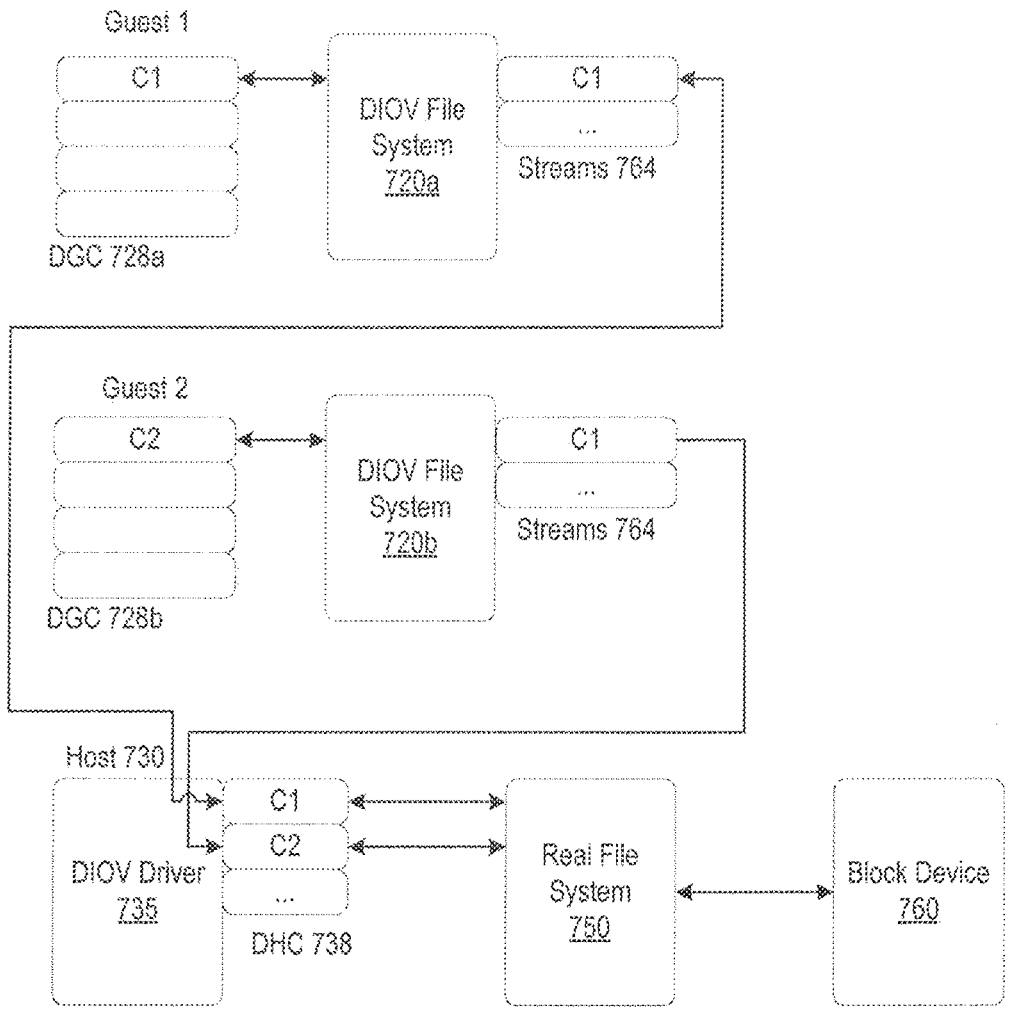
FIG. 7 illustrates exemplary shared mounts across multiple virtual machines, according to one embodiment.

As in the case of NFS, the DIOV file system can mount "DIOV storage devices" corresponding to any host directory that the host has exported to the guest(s), not just file system mount points. A special access control mechanism for DIOV is set up (similar to/etc/exports used by NFS) to control which "DIOV storage devices" may be mounted by which guests, and what permissions are offered to those mount points on those guests. DIOV storage virtualization may be referred to as "NFS over shared memory". FIG. 7 illustrates exemplary shared mounts across multiple virtual machines, according to one embodiment. A block device 760 is mounted on the host 730 using a real file system (ext4, ufs, ntfs, etc.) on a directory "/exports/astro". DIOV exports this directory "/exports/astro" as a "DIOV storage device". Guest 1 mounts this on a directory "/mnt" and Guest 2 mounts this on a directory "/projects/astro" using DIOV file system (diovfs). When guest applications try to open and read files from these mount points ("/mnt" on guest 1 or "/projects/astro" on guest 2), the DIOV file system kicks in and requests remote system calls to be performed via streams 764. The DIOV guest contexts (DGC) 728*a*-728*b* and the DIOV host context (DHC) 738 contain the EHAS and other components of the Dynamic Execution Contexts (DEC) needed to facilitate these remote system calls.

Figure 9:
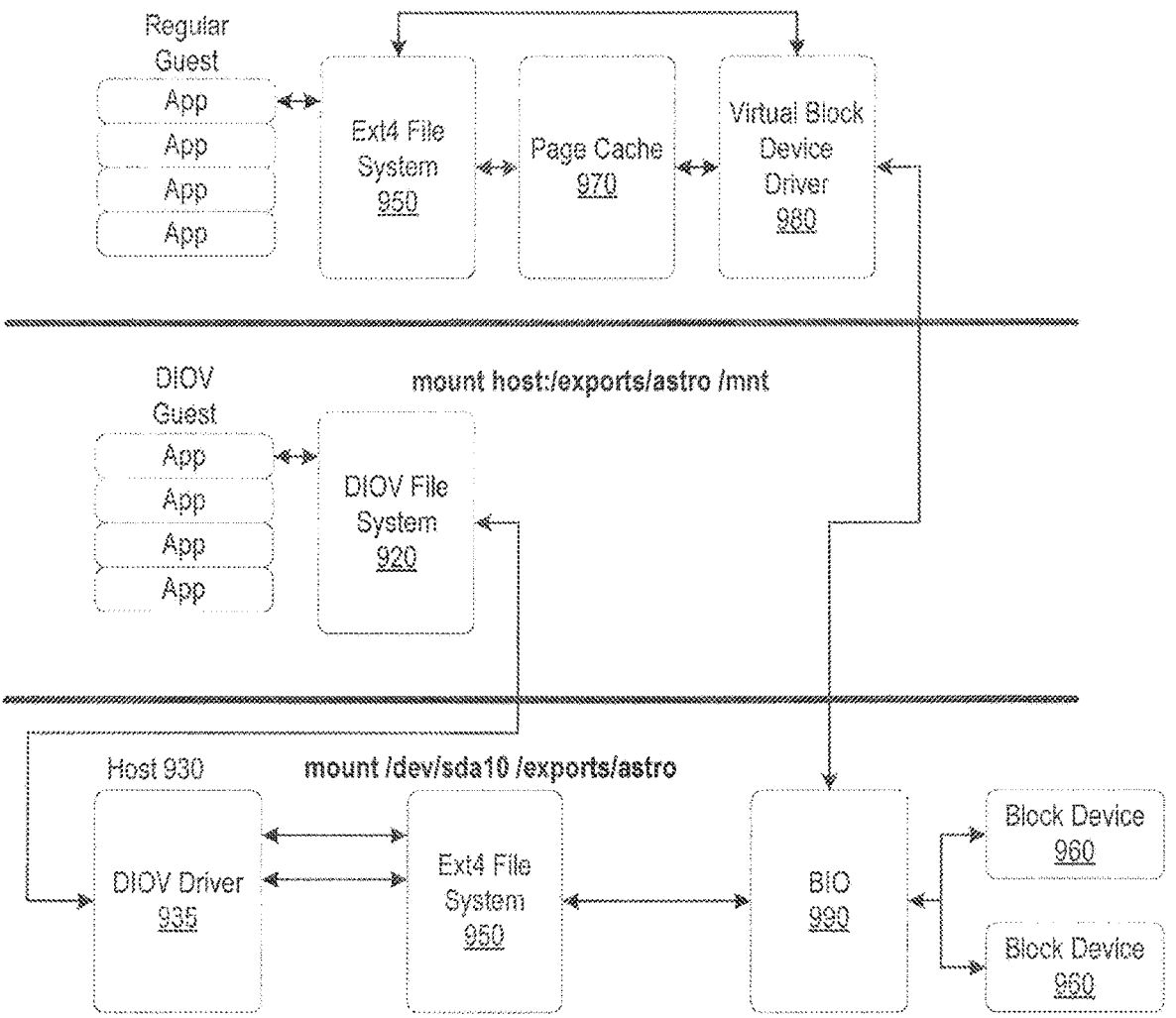
FIG. 9 illustrates exemplary the classical storage virtualization techniques and DIOV storage virtualization, according to one embodiment.

FIG. 9 illustrates exemplary the classical storage virtualization techniques and DIOV storage virtualization, according to one embodiment. A regular guest mounts a classical virtual block device using a virtual block device driver 980 as an ext4 file system 950 on a directory in the guest (say, "/mnt"). This facilitates for all caching facilities 970 offered by classical file systems 950 like the page cache, directory cache, inode cache etc. The virtual block device driver 980 performs the host I/O operations through the block I/O driver 990 to the real block device 960 on the host 930. The DIOV guest mounts a device named "host:/exports/astro" on a directory "/mnt" on the guest using the DIOV file system 920. The DIOV storage device "host:/exports/astro" is the exported host directory corresponding to the mount point of a block device 960 mounted using the ext4 file system 950. The guest applications in the DIOV guest raises requests for remote system calls that are intercepted by the DIOV file system 920 that directly communicates these requests to the ext4 file system driver 950 through the DIOV host driver 935. The ext4 file system driver 950 on the host also benefits from local caching (like page caching, directory/inode caching, etc.). The ext4 file system driver 950 eventually work with block I/O driver 990 that performs the I/O operations on the block device 960.

The DIOV storage virtualization manifests itself in two tiers (a) a core DIOV technology and (b) DIOV storage caching. The core DIOV technology enables (1) fast command initiation between a guest and a host, and (2) a zero copy I/O operation where virtual addresses of a guest user application (that originated the I/O operation) can directly be dereferenced by a host kernel driver while performing the I/O operation. The DIOV storage caching uses a shared page cache across multiple VMs, and a single open copy of a file is shared across guest processes across multiple VMs. The DIOV storage caching is implemented with no hardware cost.

DIOV Storage Cache

The DIOV host PMM driver formats a portion of the memory in the DIOV device as a storage cache. The DIOV memory as a whole is mapped into the address space of each process that performs DIOV I/O operations. This memory map includes a shared page cache that is available for access by the DIOV file system driver in the context of a guest process. In one of the embodiments, the shared page cache is organized as a set-associative cache, and maps data as large fixed size blocks to improve temporal and spatial locality of references. For example, if the block size is 64 KB, then it can factor in approximately 4 times temporal locality of references for reads and writes, in the case of a typical database applications where block size is 16 KB. The self-associative cache architecture is an implementation choice, and it is understood that other architectures based on binary trees, hash tables, sorted arrays, etc. may be employed without deviating from the scope of the present disclosure.

There are some unique properties of the DIOV storage cache. The first advantage of DIOV storage is that no extra hardware is required when using the software emulation of DIOV device. A portion of the system memory is pre-allocated by the DIOV PMM in the hypervisor or host operating system, and a portion of the DIOV memory is used for storage caching. This cache can be large in size (e.g., 500 GB). The DIOV storage cache combines the advantages of the high speed of DRAM and the large capacity of SSD caches.

The second advantage of the DIOV storage cache is that DIOV shared page cache that is transparently shared across domains does not know about the existence of each other. A single open copy of a file can be read from or written to by all guest processes (across all guests). On a single computer, coherency is enforced by the shared memory architecture, for example, a hardware coherency fabric in the computer's memory management unit (MMU). The DIOV storage cache can work across multiple physical servers (computers), and PMM assumes the responsibility of managing the coherency across the multiple physical computers.

The DIOV overcomes the challenges associated with the use of a single open copy of a file. Each process has a file descriptor for each copy of files it opens. The DIOV drivers map these per-process file descriptors to a global file descriptor. The per-process file descriptors maintain the access controls, for example, whether a file is opened read-only or read-write, whether the file is opened in a synchronous I/O or a direct I/O mode. The DIOV file system driver receives I/O requests from the guest processes and performs the operation on the shared cache honoring the semantics of file operations demanded by the file descriptors.

The third advantage of DIOV storage cache is that it honors all operating system contracts. Depending on whether a file is opened with a synchronous read/write (e.g., Linux O_SYNC) or a direct read/write (e.g., Linux O_DIRECT), the opened file is handled differently. For all intents and purposes, the DIOV storage cache behaves as the operating system's page cache but is transparently shared across multiple VMs. When a file is opened with O_SYNC, in addition to updating the cache, the system call waits for the data to be written to or read from the destination storage device. When a file is opened with O_DIRECT, the cache is invalidated, and writes and reads directly operate on the destination storage device-such files are never cached by DIOV.

The fourth advantage of DIOV storage cache is that it provides a Quality-of-Service (QoS) option to indicate that cache blocks for a particular file need to be persisted at all times in the storage cache. To provide the QoS, DIOV implements (a) a whitelist of file path names, (b) a flag (e.g., O_ALWAYSCACHED) with an open system call (e.g., Linux open(2)), or (c) a special argument passed to a read/write system call. This is beneficial for database applications where particular tables and records are hot and frequently accessed.

The fifth advantage of DIOV storage cache is that "Active writebacks" ensure that all write operations are sent to a destination storage device as soon as they are initiated by a guest process. However, the guest process that initiated the write does not wait for the write operation to complete. The data is written immediately to the write buffer (of the storage cache), and the guest process resumes the execution. This ensures (a) faster throughput for the guest process that initiated the write operation, and (b) the destination storage is rendered as consistent as it would be in the absence of the DIOV storage caching.

The sixth advantage of the DIOV storage cache is that it has a read cache and a write buffer that are seamlessly integrated into a single cache unit. Typically, the read cache and write buffer are architecturally separate for storage caching. The write buffer of the DIOV storage cache includes blocks in the cache that are dirty-only (not read from a disk before writing). Thus, the DIOV storage cache does not require a "read-for-ownership" (RFO) to be coherent. Blocks that are dirty-only (blocks of a write buffer) are not treated differently than blocks that are read; just the dirty-only blocks record the start and end offsets of the valid range of data in the cache block. The write buffer enables efficient snooping of data corresponding to writes that are in flight by virtue of active writeback. The cache manager ensures that a dirty block is not reclaimed till all write operations on the block are committed to the destination storage device.

The seventh advantage of the DIOV storage caches is that they can be extended across multiple physical computers on the system. The DIOV storage cache has the following characteristics. The cache blocks are globally indexed across physical systems. All computers maintain set-associative mappings across different physical systems. The set-associative mappings are limited to the blocks that they access. DIOV uses a fast proprietary network protocol to accesses remote cache blocks faster than accessing from a remote storage device (such as a NAS). Once a reference is resolved from a cache in a neighboring computer, the data is transferred and cached locally. When a node writes to a block, it is globally invalidated across all nodes. The coherency traffic for invalidations is kept to a minimum because of the fast network protocols used for DIOV. The shared caches across physical systems can span both direct attached storage (DAS) or network attached storage (NAS) devices.

Consistency of writes with respect to reads ensures that all current readers finish reading before overwriting a block. According to one embodiment, the consistency of writes is maintained with multiple types of locking, for example, a set level locking, and a block level locking. In both cases, a multi-level locking scheme is used. Once a reader has acquired a read lock, other readers can simply decrement the reference counts (like a semaphore), and all readers have to exit the block (i.e., block and set locks have to count up to 0) before the read lock can be relinquished (and set/block become unlocked), and a writer can grab an exclusive write lock.

|  |  |
|---|---|
| ... | |
| | −3 (Four readers) |
| | −2 (Three readers) |
| | −1 (Two readers) |
| Read Lock | : 0 (One reader) |
| Unlocked | : 1 |
| Write Lock | : 2 |

Direct attached storage (DAS) devices such as spindle hard disks, solid-state disks (SSD) can be unconditionally controlled through the DIOV storage caching. When files are accessed over a network-attached storage (NAS), NFS poses strict conditions to caching. The DIOV addresses the caching conditions of NFS in a case to case manner.

In the first case, if it can be ascertained that a NFS mount is used only by DIOV drivers across multiple physical computer system (e.g., a user assertion), the DIOV cross-domain coherency protocol is sufficient to keep the DIOV storage caching coherent across the different computers. In the second case, many files like virtual disks (e.g., vmdk, qcow2) that are used exclusively by virtual machines on a server can be mounted, cached, and shared across multiple VMs on the same server. The user declares a whitelist of files from a NAS that can be shared through the DIOV storage cache. In the third case, a DIOV host (server) is used as a sentinel node. The NAS device is mounted on the sentinel node using an NFS driver. The mount point is exported as a "DIOV storage device". The DIOV host driver on this particular host has a global visibility over all read/write requests from all other DIOV hosts that mount this "DIOV storage device". When the sentinel DIOV host driver finds a write to a block that has been cached by any of the DIOV hosts (including itself), it sends a request to those hosts to invalidate that block before it performs a write operation. Thus, the DIOV host driver on the sentinel node ensures coherency across all operations on the NAS device. Alternately, a DIOV-aware NFS driver can coherently monitor read/write requests from both DIOV as well as non-DIOV hosts.

Since DIOV storage cache operations transparently snoop the write buffers, the DIOV cache manager gives a priority for evictions and cache fills (read from disk) over active writeback. This improves response times for reads, especially on a slow storage device. However, since the prioritized evictions and cache fills can have an impact on the consistency of the destination storage device, the optimization of evictions and cache fills is performed only on a user assertion when it is determined to be safe. A similar optimization can be performed (also under a user assertion) is "write combining". When writes occur to contiguous memory locations in a dirty-only block, the DIOV driver combines all those writes into a single write operation to the destination storage driver. Write-combining can occur on regular dirty blocks also where the writes are to non-contiguous locations.

Memory mapping of files (e.g., Linux mmap(2)) is treated distinctly in the DIOV file system virtual driver. Mmap is integrated into the DIOV storage cache architecture. Page faults cause cache fills, while page evictions cause page table mappings to be removed. Munmap removes page table mappings and VMAs but does not disturb the data in the caches since the data may be used by other processes across various guests.

The present system and method provides intelligent cache eviction to ensure that hot blocks actually get time to warm up in the cache. When the cache fills up, the DIOV cache manager evicts a fixed number of blocks (e.g., 10% of blocks) based on their age, total reference counts, and the time of last reference and adds the evicted blocks to a free list. The blocks that are evicted are the coldest blocks. Hence, blocks that are genuinely most frequently used get warmed up over a period of time and persist even over reboots. The large size of the DIOV storage cache also ensures that hot blocks are not evicted under pressure.

In one embodiment, a disk (e.g., a spindle hard disk or a solid state disk) is devoted to persist a history of the hottest blocks identified by the DIOV storage cache, across reboots. Only the names of the files, and the offset and size of the hot blocks need to be persisted, and hence the persistence does not involve too much of overhead. Over a period of time, the caches saturate with hot blocks, and the performance sustains at a high level even across reboots.

Figure 6:
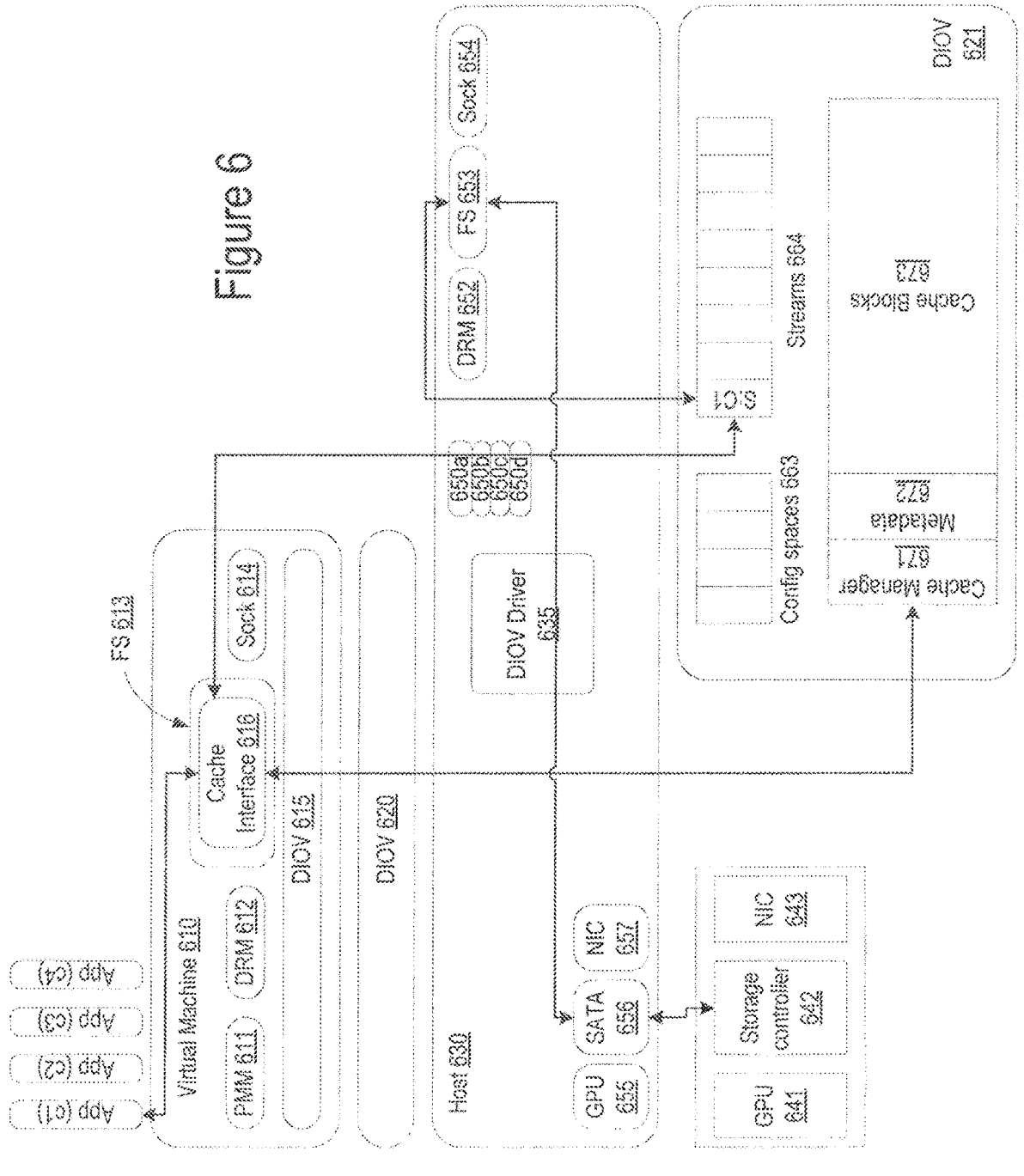
FIG. 6 illustrates an exemplary architecture of the DIOV storage cache, according to one embodiment.

FIG. 6 illustrates an exemplary architecture of the DIOV storage cache, according to one embodiment. The DIOV file system virtual driver 613 manages references to the host mounted file system and block device. The cache interface 614 therein, redirects all reads, writes, mmap, fsync, etc. to the shared cache. All other operations (e.g., open, close, operations on directories, links, etc.) are performed through streams. The cache manager 671 maintains the cache parameters and configuration information shared across the guest and the host. The metadata 672 comprises of many data structures including the sets and ways of the set-associative cache, string table to uniquify pathnames referenced during file operations, etc. The huge bulk of the DIOV storage cache is used to hold the actual data blocks 673 referenced by the set-associative cache.

Figure 8:
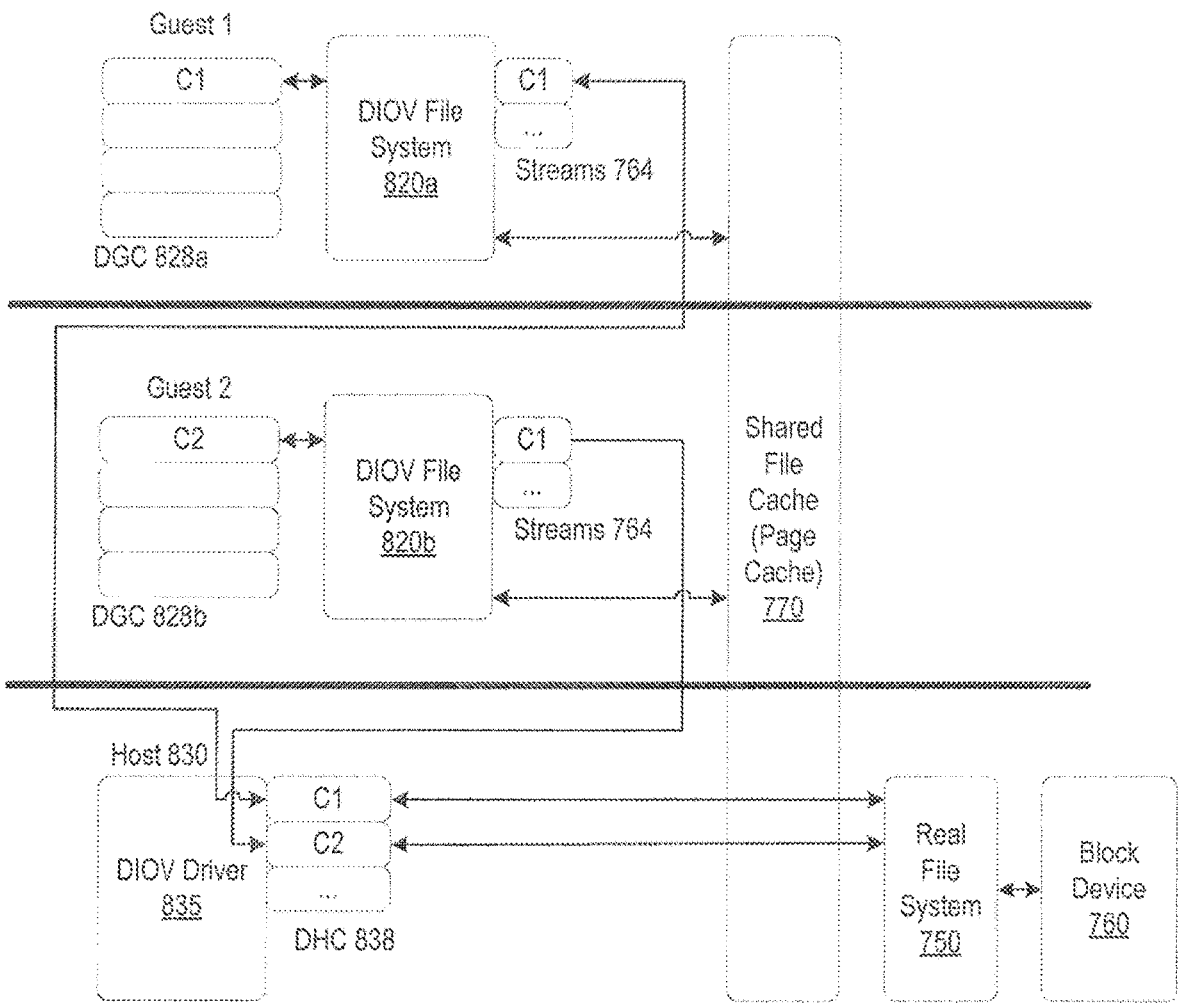
FIG. 8 illustrates hot and cold operations, according to one embodiment.

FIG. 8 illustrates hot and cold operations, according to one embodiment. A DIOV storage device (say, "host:/exports/astro") is mounted on Guests 1 and 2 via the DIOV file system 820a-820b. Hot operations like reads, writes, mmaps, and fsync are redirected to the shared page cache 770. Other operations including opening and closing of files, and managing directories, links, etc. are redirected to the host DIOV file system driver 835 through streams 764. The page cache is efficiently shared across applications on multiple guest operating systems (or virtual machines).

In the above illustrations, the DIOV storage cache is treated as a single cache shared across multiple VMs. According to one embodiment, the DIOV storage cache can be implemented as a system of segregated caches (one for each VM, or one for each file system, or one for each file system per VM, etc.) while preserving the benefit of sharing across VMs. The DIOV provides special APIs for cache-to-cache communication to allow a user process to peek into (or wink in) blocks that belong to caches of other VMs. The cache-to-cache communication is possible because the entire DIOV memory is mapped into the address space of all processes of all VMs.

The following illustration assumes an inclusive cache (all blocks referenced have to be in cache), and active writeback is instantaneous. However, DIOV is not limited to these implementation choices. For example, (a) cache misses may result in direct operations on the backing storage devices without a cache fill, (b) writes may not trigger an immediate writeback, but the "active writeback" thread may scour through dirty blocks in the DIOV cache and write them to backing storage devices asynchronously, (c) the support for dirty-only blocks may be optional. The host DIOV driver may employ a profiling mechanism to determine which files/blocks are hot before deciding to promote them to the DIOV storage cache.

Figure 10:
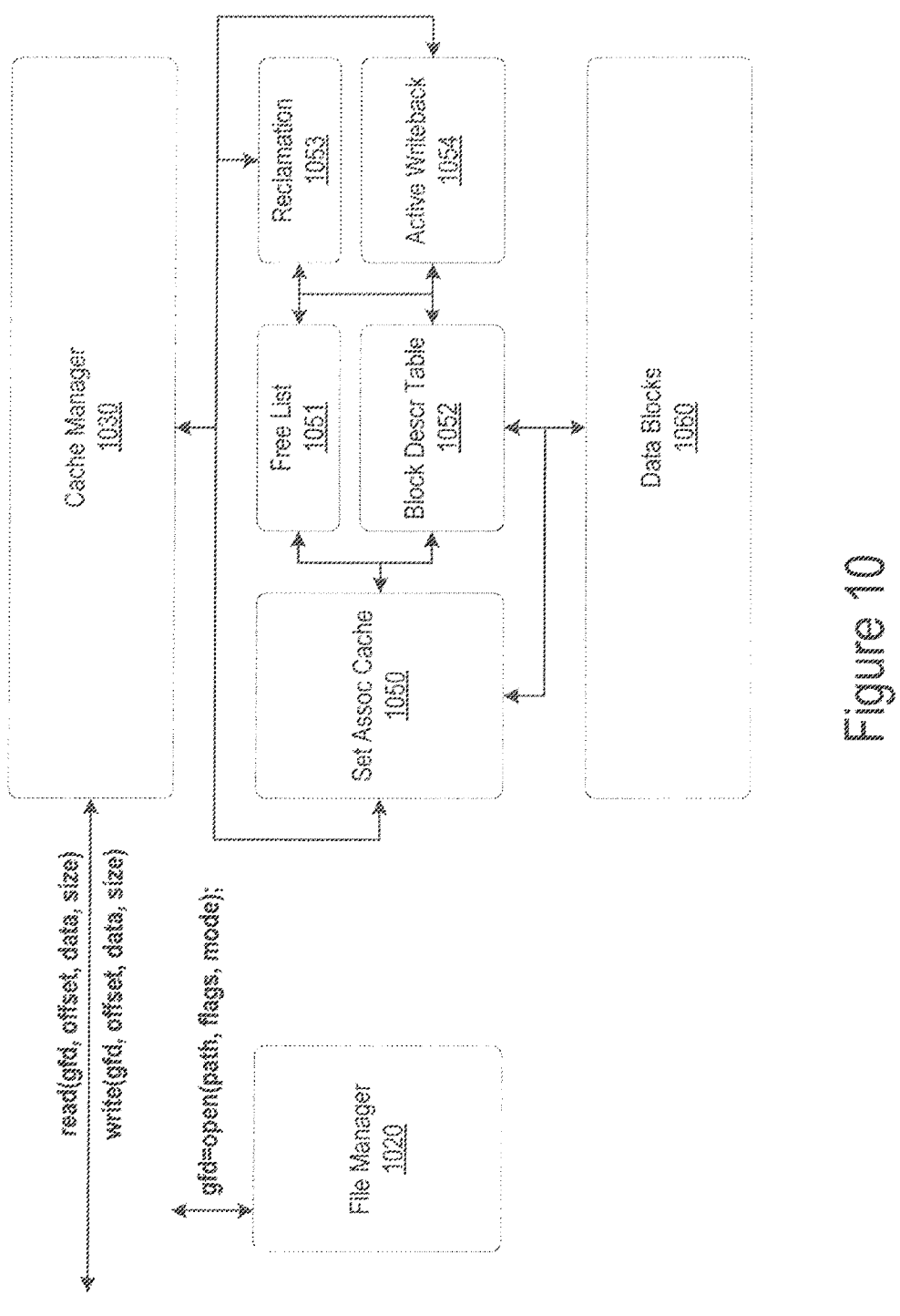
FIG. 10 illustrates a block diagram of an exemplary DIOV storage cache, according to one embodiment.

FIG. 10 illustrates a block diagram of an exemplary DIOV storage cache, according to one embodiment. When a guest process opens a file, the DIOV file system driver hands over the request to a file manager 1020 on the host. The file manager on the host identifies whether the file is already opened on the host. If the file is opened, the file manager returns the global file descriptor (GFD). The DIOV file system driver on the guest builds a map of the per-process file descriptor opened by the guest process to the global file descriptor of the file on the host. The per-process file descriptor is returned to the guest process.

When the process initiates an I/O operation with its (per-process) file descriptor, the DIOV file system driver confirms that (a) the file descriptor has the right permissions to perform the operation, and (b) caching is permitted for file operations on this file descriptor (for example, not opened for direct I/O). The I/O requests on the per-process file descriptors are translated into an I/O operation on the global file descriptor (gfd), and the request is handed over to the cache manager.

The cache manager 1030 determines the block corresponding to the specified global file descriptor and the specified offset by looking up in the set associative cache 1050 with set=f(gfd, offset, hash), where "hash" is originally set to zero. If the cache manager 1030 finds a hit in the cache, the operation is directly performed with appropriate locking; reads are free, and the read counter is decremented to indicate one more reader is active; writes wait until all current readers exit the set and the way (or block) and obtain a write lock. If the operation is a write, the block is marked "dirty" and a write is immediately initiated to the destination storage device. However, the guest process does not wait for the completion of the write.

If the cache manager 1030 fails to find a hit in the cache, for a write operation, a new block is created and the corresponding block descriptor is marked "dirty-only". The data is copied onto the block, and the valid bounds are recorded in the block descriptor for the data block. A write is immediately initiated to the destination storage device. However, the guest process does not wait for the completion of the write. For a read operation, a new block is created and is filled from the destination storage device. If a new block was not available for the read or write miss, the cache manager 1030 is notified, and the reclamation service 1053 is started. This frees up a specific number of blocks (e.g., 10% of blocks) picking the coldest ones first, cleans up the cache ways that originally contained these blocks, and adds these blocks into the free list 1051. If all the ways of a particular set are exhausted, the particular set is rehashed into a new set=f(gfd, offset, hash), where "hash" is determined by another function of current set and gfd, g(set, gfd).

An active writeback manager 1054 in the background continuously cleans up dirty pages by performing a write to the destination storage device as soon as it is cached in the

Figure 12:
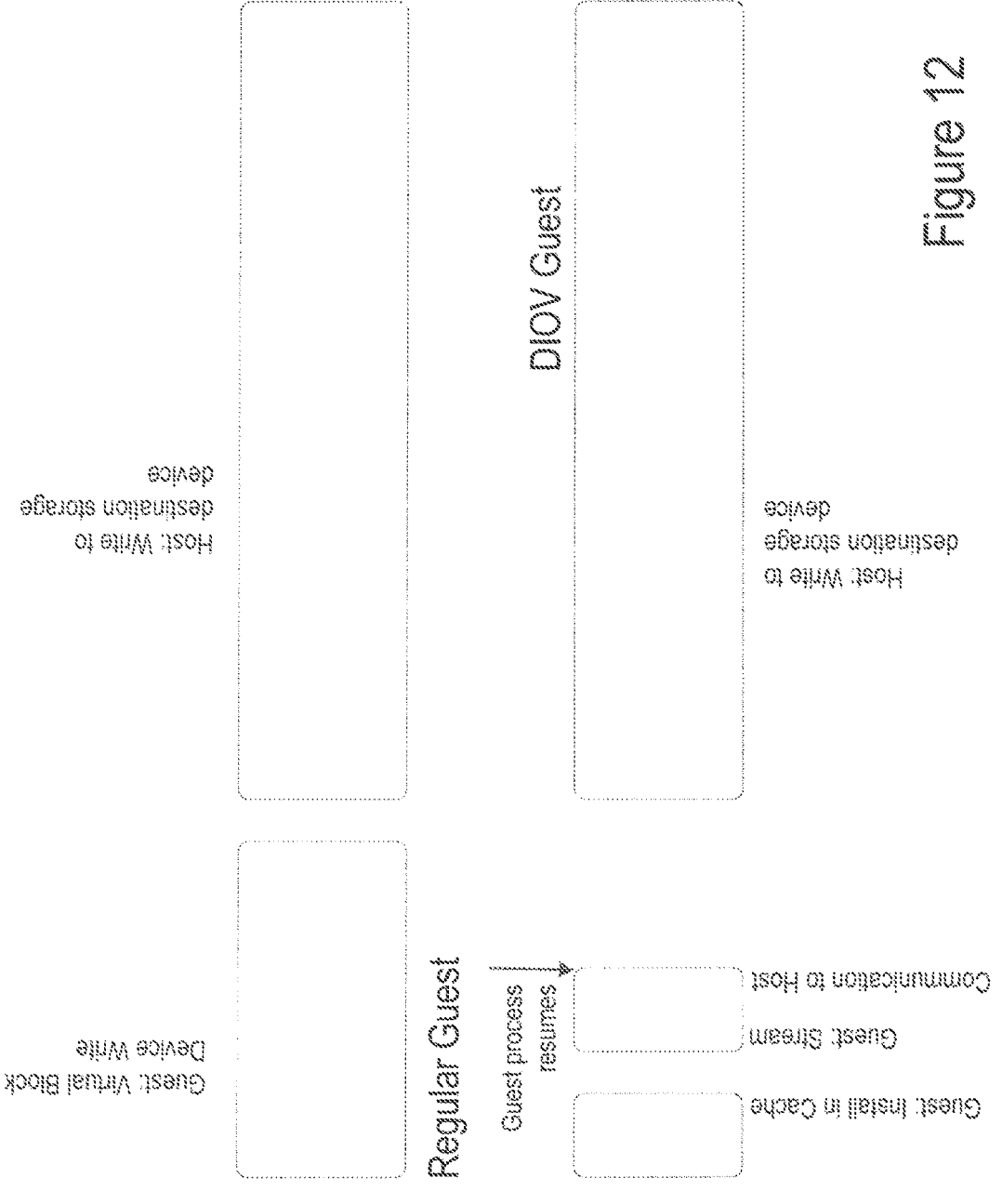
FIG. 12 illustrates the process of an active writeback, according to one embodiment.

30 write buffer (of the storage cache). This ensures that even in the case of an emergency shutdown, and the destination storage device will be consistent. FIG. 12 illustrates the process of an active writeback, according to one embodiment. The top half shows the behavior of writes on a non-DIOV host. The writes to the virtual block devices in the guest is converted by the host into an actual write to the destination storage device. The bottom half shows the behavior on the DIOV host. The guest DIOV file system driver first updates the cache (write buffer), then immediately sends a write request to the host over its stream, and the host immediately performs a write to the destination device. However, the guest process resumes after it has successfully initiated the stream request for the write.

DIOV API (Application Binary Interface)

Conventional cloud management in a data center and a cloud infrastructure involves several layers (or tiers) of abstraction each with its own APIs, such as (1) cloud applications (e.g., management consoles, OpenFlow), (2) cloud platform management (e.g., Scalr), (3) cloud management platforms (e.g., Openstack, Cloudstack, Eucalyptus, Open Nebula, vCloud), (4) virtual drivers for storage, networking, and graphics in guest OS running on virtual machines, (5) hardware abstraction embodied by virtual machines, (6) native drivers running on host (or Dom0 if using Xen Hypervisor), (7) hypervisors (e.g., Xen, KVM, VMware, Hyper-V), and (8) hardware.

Conventional virtualization optimization aims at providing a fast I/O path between tiers 4 and 6. However, the present DIOV directly reduces the height of any abstraction layer. The DIOV APIs (built into a DIOV SDK) enables I/O requests from tiers 1 (or 2 or 3) to go directly to tier 6. The DIOV API elevates the storage/networking/graphics I/O and dynamic memory allocation (e.g., shared heap) primitives directly into any application that wishes to benefit from hardware speeds. Therefore, DIOV can be applied to high performance computing (HPC) and high availability (HA) applications that are running on the guests and require intimate knowledge and extremely fast interaction with the hardware devices and their native device drivers.

For simplicity, tiers 1, 2, and 3 in the above example may be combined together to be any native application running on the guest. For best results, applications may be rewritten to include DIOV API calls in the appropriate places. It is conceivable to provide a legacy bridge so that existing programs (without recompilation) can tap into DIOV API's through indirect methods such as Linux LD_PRELOAD, and Windows Detours, where library functions (or system calls) in the unmodified applications can be redirected to new re-implementations of these functions inside the DIOV libraries.

The user space DIOV API (where DIOV operations are initiated by the guest user space API) and the legacy mode DIOV (where DIOV operations are initiated through kernel mode drivers) can co-exist. The DIOV API has a performance benefit because the DIOV API bypasses a guest kernel to perform performance critical operations (e.g., read and write operations), and directly interfaces with the host kernel to perform these operations.

Figure 11:
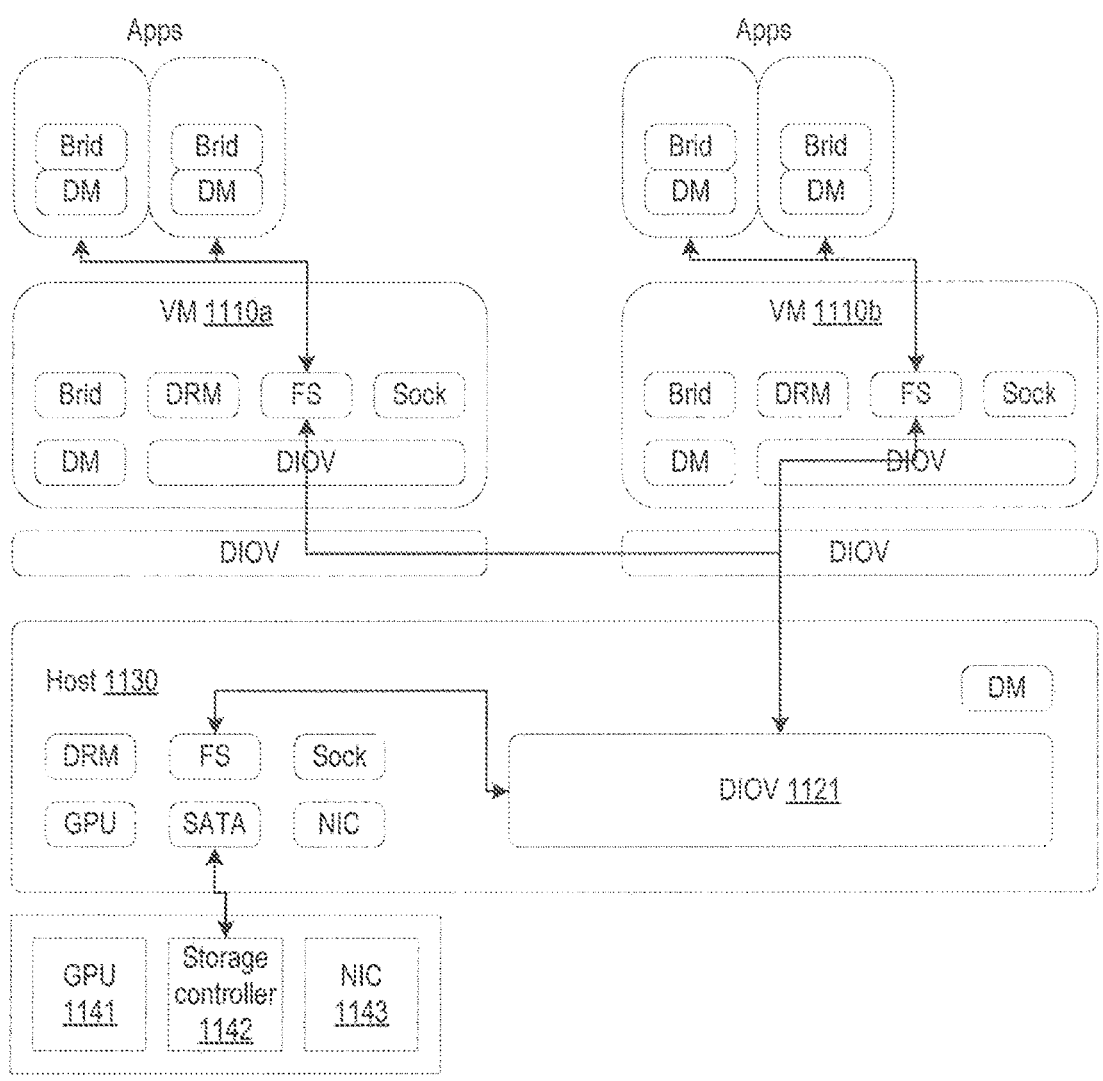
FIG. 11 illustrates a block diagram of an exemplary DIOV including a bridge code and a DIOV memory, according to one embodiment.

To ensure that the DIOV API and the legacy mode DIOV can co-exist, several functionalities are shared between the guest kernel and guest user space API including the DIOV storage cache interface, and DIOV shared heap interfaces. To facilitate easy sharing of these functionalities, both DIOV API and DIOV guest kernel drivers are allowed to execute code for these functionalities from a common source. This code, herein referred to as "bridge code" is specially designed to be completely self-contained, position independent (and hence relocatable), and re-entrant (i.e., multiple threads across user and kernel space can simultaneously execute the code). The "bridge code" can reside anywhere. For example, it could reside inside DIOV Memory. The guest PMM driver will map this code into the address space of the guest kernel as well as into the address space of guest applications. Both the guest driver and the user space DIOV API library resolve the pointers to functions in the bridge code, and save them for subsequent invocation of the bridge code from the kernel space or user space. The data that the bridge code operates on, resides in the DIOV memory (e.g., data structures for the DIOV storage cache, DIOV shared heap). FIG. 11 illustrates a block diagram of an exemplary DIOV including a bridge code and a DIOV memory, according to one embodiment. The bridge code and the DIOV memory (DM) co-exist in the guest kernel (DIOV driver) space as well as the guest user (DIOV API) space. In the context of native operating systems, the bridge code (Brid) can reduce system call overheads, where the kernel can offload performance critical chores to be performed in the user space.

Security of DIOV

In guest and host systems, the DIOV memory is mapped into the user address space of each process that performs storage, networking, or graphics operations. Additionally, the DIOV memory has the following characteristics. Only DIOV driver knows the exact location in the user address space where the DIOV memory is mapped (in the EHAS). The DIOV memory is mapped into the guest EHAS with the 'user/system' bit set to zero; only the kernel components (CPL=0) can access these pages for reading or writing. This makes it impossible for a user space component to intentionally or otherwise corrupt the DIOV memory and cause DIOV to fail. The DIOV memory is mapped only into the EHAS, so normal guest operations such as memory mapping (Linux mmap(2)) cannot inadvertently corrupt the DIOV memory. If malicious software uses a kernel driver, it needs access to the EHAS to be able to corrupt the DIOV memory. Since the EHAS is deeply embedded inside the DIOV guest context (DGC) for the process, it is difficult or impossible to be intercepted. The user is advised about the consequence of using the assertion on a "well behaved" program. The only time when the DIOV memory (and the rest of EHAS VMAs) is visible in the normal guest context is when the user asserts that the processes in a guest are "well-behaved" (even then only to kernel drivers). However, most data centers maintain a high level of control over software installed in the guest VMs. Without administrator privileges, installation of kernel modules (or drivers) are impossible and hence even this assertion is of a minor consequence to security and reliability of DIOV. DIOV does not touch any data structure on the guest or host, except through published (and exported) user space and kernel interfaces, hence the possibility of DIOV drivers corrupting a guest kernel is minimal. Some critics may consider DIOV itself to to be a malware because they believe DIOV grabs control of I/O operations unbeknownst to the guest kernel and user applications. This is untrue because the users (typically administrator) has to enable specific interfaces before DIOV based I/O virtualization is enabled. For example, in the case of storage virtualization, only if a "DIOV storage device" is mounted on the guest using DIOV file system driver, the DIOV storage virtualization is enabled on the guest (and that too only for that mount point or directory).

The above example embodiments have been described herein above to illustrate various embodiments of implementing a system and method for providing dynamic device virtualization. Various modifications and departures from the disclosed example embodiments will occur to those having ordinary skill in the art. The subject matter that is intended to be within the scope of the present disclosure is set forth in the following claims.

I claim:

1. A system, comprising:
a host computer having an input output virtualization driver, and a host memory;
a guest computer having a guest file system; and
an emulated input output virtualization device running on the host computer, the emulated input output virtualization device comprising allocated streams, configuration spaces, and a process and memory manager (PMM), wherein the PMM is configured to: (i) format the host memory for use by the emulated input output virtualization device and (ii) manage a dynamic execution context (DEC) to complete a remote input output operation from the guest file system.

2. The system of claim 1, wherein the host memory is formatted by the PMM for input output memory optimization functions.

3. The system of claim 1, wherein the PMM integrates the host memory into an address space of each guest process running on the guest computer.

4. The system of claim 1, wherein the PMM keeps track of the host computer's memory consumption.

5. The system of claim 1, wherein the PPM is configured to determine whether the host computer is running below a critical level of memory.

6. The system of claim 5, wherein the PMM reclaims memory assigned to the PMM and provides the reclaimed memory to the host computer.

7. The system of claim 1, wherein the PMM is configured to format host memory into at least one of streams, configuration spaces, a shared storage cache, or a shared heap.

8. The system of claim 1, wherein the emulated input output virtualization device operates a private interface understood by the host input output virtualization driver.

9. A system, comprising:
a host computer having an input output virtualization driver, and a host memory;
a guest computer having a guest file system; and
an emulated input output virtualization device running on the host computer, the emulated input output virtualization device comprising allocated streams, configuration spaces, and a process and memory manager (PMM), wherein the PMM is configured to allocate a chunk of host memory to the emulated input output virtualization device and manage a dynamic execution context (DEC) to complete a remote input output operation from the guest file system.

10. The system of claim 9, wherein the host memory allocated by the PMM is transparent to the host computer.

11. The system of claim 9, wherein the PPM is configured to releases memory not used by the emulated input output virtualization device for use by the host computer.

12. The system of claim 9, wherein the PPM is configured to automatically relinquish memory for consumption by the host computer.

13. The system of claim 9, wherein the host memory is formatted by the PMM for input output memory optimizations.

14. The system of claim 9, wherein the PMM integrates the host memory into an address space of each guest process running on the guest computer.

15. The system of claim 9, wherein the PPM keeps track of the host computer's memory consumption.

16. The system of claim 9, wherein the PPM is configured to determine whether the host computer is running below a critical level of memory.

17. The system of claim 16, wherein the PMM reclaims memory assigned to the PMM and provides the reclaimed memory to the host computer.

18. The system of claim 9, wherein the PMM is configured to format the host memory allocated to the emulated input output virtualization device into at least one of streams, configuration spaces, a shared storage cache, or a shared heap.

19. A computer-implemented method, comprising:

providing a host computer having an input output virtualization driver, and a host memory, wherein the input output virtualization driver includes a process and memory manager (PMM);

emulating an input output virtualization device on the host computer;

allocating a portion of the host memory during a boot phase for exclusive use by the emulated input output virtualization device;

formatting the portion of host memory for use by the emulated input output virtualization device;

determining whether the memory consumption of the host computer is below a critical level;

reclaiming the portion of the host memory allocated to the emulated input output virtualization device; and allocating the reclaimed host memory to the host computer.

20. The method of claim 19 wherein reclaiming the portion of the host memory allocated to the emulated input output virtualization device is performed subsequent to determining whether the memory consumption of the host computer is below a critical level.

21. The method of claim 19, wherein allocating the reclaimed host memory to the host computer is performed subsequent to reclaiming the portion of the host memory.

22. The method of claim 19, further comprising:

managing a dynamic execution context (DEC) to complete a remote input output operation from a guest file system of a guest computer, wherein the emulated input output virtualization device manages the DEC.

23. The method of claim 19, wherein the host memory is formatted by the PMM for input output memory optimization functions.

24. The method of claim 19, further comprising:

integrating the host memory into an address space of each guest process running on a guest computer, wherein the host memory is integrated by the PMM.

25. The method of claim 19, wherein formatting the portion of host memory comprises formatting the portion of the host memory into at least one of streams, configuration spaces, a shared storage cache, or a shared heap.

26. The method of claim 19, further comprising:

operating a private interface understood by the host input output virtualization driver, wherein the private interface is operated by the emulated input output virtualization device.

27. The method of claim 19, wherein the PMM allocates the portion of the host memory for exclusive use by the emulated input output virtualization device.

28. The method of claim 27, wherein the portion of the portion of the host memory allocated by the PMM is transparent to the host computer.

29. The method of claim 19, wherein allocating the portion of the host memory comprises allocating a chunk of host memory to the emulated input output virtualization device.

30. The method of claim 19, further comprising:

tracking memory consumption of the host computer, wherein the memory is tracked by the PMM.

* * * * *